US010149866B2

(12) United States Patent
Sidhu et al.

(10) Patent No.: US 10,149,866 B2
(45) Date of Patent: Dec. 11, 2018

(54) COMPOSITIONS AND METHODS FOR TREATING OR PREVENTING OXALATE-RELATED DISEASE

(71) Applicants: OxThera Intellectual Property AB, Stockholm (SE); The Milton J. Allison Revocable Trust, Ames, IA (US)

(72) Inventors: Harmeet Sidhu, Gainesville, FL (US); Milton J. Allison, Ames, IA (US)

(73) Assignees: OXTHERA INTELLECTUAL PROPERTY AB, Stockholm (SE); THE MILTON J. ALLISON REVOCABLE TRUST, Ames, IA (US)

( * ) Notice: Subject to any disclaimer, the term of this patent is extended or adjusted under 35 U.S.C. 154(b) by 462 days.

(21) Appl. No.: 13/919,266

(22) Filed: Jun. 17, 2013

(65) Prior Publication Data
US 2014/0030324 A1 Jan. 30, 2014

Related U.S. Application Data

(63) Continuation of application No. 10/868,242, filed on Jun. 15, 2004, now Pat. No. 8,486,389.

(51) Int. Cl.
A61K 9/48 (2006.01)
A61K 35/74 (2015.01)
A61K 38/44 (2006.01)
A61K 38/45 (2006.01)
A61K 38/51 (2006.01)
A61K 38/54 (2006.01)
A61K 45/06 (2006.01)

(52) U.S. Cl.
CPC .............. A61K 35/74 (2013.01); A61K 38/44 (2013.01); A61K 38/443 (2013.01); A61K 38/45 (2013.01); A61K 38/51 (2013.01); A61K 38/54 (2013.01); A61K 45/06 (2013.01); C12Y 102/03004 (2013.01); C12Y 208/03016 (2013.01); C12Y 401/01002 (2013.01); C12Y 401/01008 (2013.01)

(58) Field of Classification Search
None
See application file for complete search history.

(56) References Cited

U.S. PATENT DOCUMENTS

| | | | |
|---|---|---|---|
| 4,205,132 A | 5/1980 | Sandine et al. | |
| 4,539,118 A | 9/1985 | Crider | |
| 4,619,897 A | 10/1986 | Hato et al. | |
| 5,206,219 A | 4/1993 | Desai | |
| 5,263,992 A | 11/1993 | Guire | |
| 5,286,495 A * | 2/1994 | Batich et al. | 424/490 |
| 5,427,935 A | 6/1995 | Wang | |
| 5,547,870 A | 8/1996 | Datta et al. | |
| 5,554,147 A | 9/1996 | Batich et al. | |
| 5,603,971 A | 2/1997 | Porzio et al. | |
| 5,604,111 A | 2/1997 | Peck | |
| 5,607,417 A | 3/1997 | Batich et al. | |
| 5,788,687 A | 8/1998 | Batich et al. | |
| 5,868,720 A | 2/1999 | Van Antwerp | |
| 5,912,125 A | 6/1999 | Peck et al. | |
| 6,033,719 A | 3/2000 | Keogh | |
| 6,033,888 A | 3/2000 | Batich et al. | |
| 6,080,404 A | 6/2000 | Branham et al. | |
| 6,090,628 A | 7/2000 | Peck et al. | |
| 6,153,252 A | 11/2000 | Hossainy | |
| 6,177,478 B1 | 1/2001 | Holmes-Farley et al. | |
| 6,200,562 B1 | 3/2001 | Sidhu et al. | |
| 6,203,797 B1 | 3/2001 | Perry | |
| 6,214,980 B1 | 4/2001 | Peck et al. | |
| 6,281,252 B1 | 8/2001 | Holmes-Farley et al. | |
| 6,297,425 B1 | 10/2001 | Schelonge et al. | |
| 6,355,242 B1 | 3/2002 | Sidhu et al. | |
| 6,566,407 B2 | 5/2003 | Holmes-Farley et al. | |
| 6,699,469 B2 | 3/2004 | Sidhu et al. | |
| 6,929,940 B1 | 8/2005 | Richards et al. | |
| 7,407,668 B2 | 8/2008 | Shephard | |
| 8,431,122 B2 | 4/2013 | Sidhu et al. | |
| 8,486,389 B2 | 7/2013 | Sidhu et al. | |
| 8,545,836 B2 | 10/2013 | Kaul et al. | |
| 8,900,575 B2 | 12/2014 | Li et al. | |
| 8,940,295 B2 | 1/2015 | Sidhu et al. | |
| 2002/0021504 A1 | 2/2002 | Bayer et al. | |
| 2003/0138415 A1 | 7/2003 | Shephard | |
| 2007/0184118 A1 | 8/2007 | Li et al. | |
| 2008/0317810 A1 | 12/2008 | Sidhu | |
| 2010/0028422 A1 | 2/2010 | Kaul | |
| 2013/0216515 A1 | 8/2013 | Sidhu et al. | |
| 2015/0125538 A1 | 5/2015 | Li et al. | |

FOREIGN PATENT DOCUMENTS

| | | |
|---|---|---|
| DE | 3030185 | 4/1982 |
| DE | 3204284 | 8/1983 |
| JP | 9503951 | 4/1997 |
| WO | WO 95/31537 | 11/1995 |
| WO | WO 95/35377 | 12/1995 |
| WO | WO 98/07922 | 2/1998 |
| WO | WO 98/16632 | 4/1998 |
| WO | WO 1998/042827 | 10/1998 |
| WO | WO 98/52586 | 11/1998 |
| WO | WO 99/22744 | 5/1999 |
| WO | WO 00/72855 A2 | 12/2000 |
| WO | WO 00/74657 | 12/2000 |
| WO | WO 2003/042380 | 5/2003 |
| WO | WO 2004/018634 | 3/2004 |
| WO | WO 2005/123116 | 12/2005 |
| WO | WO 2008/105911 | 9/2008 |

OTHER PUBLICATIONS

Lane, B.G., Faseb J., 1994, vol. 8, p. 294-301.*

(Continued)

Primary Examiner — Kade Ariani
(74) Attorney, Agent, or Firm — Foley & Lardner LLP

(57) ABSTRACT

The present invention comprises methods and compositions for the reduction of oxalate in humans, animals and plants. For example, the invention provides methods and compositions for the delivery of one or more oxalate-reducing enzymes to the intestinal tracts of persons and animals. The methods and compositions can be used in treating and preventing oxalate-related conditions.

10 Claims, 7 Drawing Sheets

(56) References Cited

OTHER PUBLICATIONS

Hoppe et al., Am J Kidney Dis., 20011, vol. 58, No. 3, p. 453-455.*
Hoppe et al., Kidney International, 1999, vol. 56, p. 268-274.*
International Search Report for PCT Application No. PCT/US2006/047909 dated Sep. 23, 2008.
International Search Report for PCT Application No. PCT/US2006/047967 dated Oct. 6, 2008.
Grases, Felix et at., "Study on Concretions Developed Around Urinary Catheters and Mechanisms of Renal Calculi Development", Nephron, vol. 88, pp. 320-328, Aug. 2000.
Sidhu, Harmeet et al., "Direct Quantification of the Enteric Bacterium Oxatobacter Formigenes in Human Fecal Samples by Quantitative Competitive-Template PCR", Journal of Clinical Microbiology, vol. 37, No. 5, pp. 1503-1509; May 1999.
Sidhu et al., "Rapid Reversal of Hyperoxaluria in a Rat Model After Probiotic Administration of Oxalobactoer Formigenes," The Journal of Urology, vol. 166, pp. 1487-1491, Oct. 2001.
International Search Report for Related PCT Application No. PCT/US05/21134 dated Nov. 14, 2007.
Chandran, P. et al., "Improved Determination of Urinary Oxalate with Alkylamine Glass Bound Barley Oxalate Oxidase", Journal of Biotechnology, vol. 85, pp. 1-5, Jan. 2001.
Defife, Kristin M. et al., "Effects of Photochemically Immobilized Polymer Coatings on Protein Adsorption, Cell Adhesion, and the Foreign Body Reaction to Silicone Rubber", Journal of Biomedical Materials Research, vol. 44, DOS. 298-307, Mar. 1999.
Denstedt, J.D. et al., "Advances in Ureteral Stent Technology", The World Journal of Urology, vol. 18, pp. 237-242, Sep. 2000.
Denstedt, J.D. et al., "Biomaterials Used in Urology: Current Issues of Biocompatibility, Infection, and Encrustation", Journal of Endourology, vol. 12, pp. 493-500, Dec. 1998.
Ditizio, V. et al., "A Liposomal Hydrogel for the Prevention of Bacterial Adhesion to Catheters", Biomaterials, vol. 19, pp. 1877-1884, Oct. 1998.
D'Urso, E.M. et al., "Poly(Ethylene Glycol)—Serum Albumin Hydrogels as Matrix for Enzyme Immobilization: Biomedical Applications", Artificial Cells, Blood Substitute and Immobilization, Biotechnology, vol. 23. pp. 587-595, Feb. 1995.
El-Faqih et al., "Polyurethane Internal Ureteral Stents in Treatment of Stone Patients: Morbidity Related to Indwelling Times", The Journal of Urology, vol. 146, pp. 1487-1491, Dec. 1991.
Fuse, H. et al., "Crystal Adherence to Urinary Catheter Materials in Rats", The Journal of Urology, vol. 151, pp. 1703-1706, Jun. 1994.
Gaboury, S.R. et al., "Analysis of Gas Plasma-Modified Poly(dimethylsiloxane) Elastomer Surfaces: Attenuated-Total-Reflectance-Fourier Transform Infared Spectroscopy", American Chemical Society, pp. 777-790, 1993.
Gilchrist, T. et al., "Controlled Silver-Releasing Polymers and their Potential for Urinary Tract Infection Control", Biomaterials, vol. 12, pp. 76-78, Jan. 1991.
Hsiue, G.H. et al., "Surface Characterization and Biological Properties Study of Silicone Rubber Membrane Grafted with Phospholipid as Biomaterial via Plasma Induced Graft Copolymerization", J Biomed Materials Research, vol. 12, pp. 134-147 Oct. 1998.
Johnson, J.R. et al., "Prevention of Catheter-Associated Urinary Tract Infection with a Silver Oxide-Coated Urinary Catheter: Clinical and Microbiologic Correlates", Journal of Infectious Disease, vol. 162, pas. 1145-1150, Nov. 1990.
Keane, P.F. et al., "Characterization of Biofilm and Encrustation on Ureteric Stents in Viva", British Journal of Urology, vol. 73, pp. 687-691, Jun. 1994.
Kulik E. et al., "In Vitro Platelet Adhesion to Nonionic and Ionic Hydrogels with Different Water Contents", Journal of Biomed Materials Research, vol. 30, pp. 295-304, Mar. 1996.
Ko, Y.G. et al., "Immobilization of Poly(Ethylene Glycol) or its Sulfonate onto Polymer Surfaces by Ozone Oxidation", Biomaterials, vol. 22, pp. 2115-2123, Aug. 2001.

Langefeld, S. et al., "Functionally Adapted Surfaces on a Silicone Keratoprosthesis", The International Journal of Artificial Organs, vol. 22, pp. 235-241, 1999.
Lee, S.D. et al., "Characterization of Plasma-Induced Graft Polymerization of 2-Hydroxyethyl Methacrylate onto Silicone Rubber", Journal of Applied Polymer Science, vol. 54, pp. 1279-1287, 1994.
Lee, S.D. et al., "Plasma-Induced Grafted Polymerization of Acrylic Acid and Subsequent Grafting of Collagen onto Polymer Film as Biomaterials", Biomaterials, vol. 17, pp. 15991608, Aug. 1996.
Lee, S.D. et al., "Preparation and Characterization of a Homobifunctional Silicone Rubber Membrane Grafted with Acrylic Acid Via Plasma-Induced Graft Copolymerization", Journal of Polymer Science: Part A: Polymer Chemistry, vol. 34, pp. 141-148, 1996.
Mason, M. et al., "Attachment of Hyaluronic Acid to Polypropylene, Polystyrene, and Polytetrafluoroethylene", Biomaterials, vol. 21, pp. 31-36, Jan. 2000.
Mutlu, M. et al., "Matrix Surface Modification by Plasma Polymerization for Enzyme Immobilization", Journal of Materials Chemistry, vol. 1, pp. 447-450, 1991.
Nakada, S. et al., "Hyperbranched Modification of Unsaturated Side Chains of Polyethylene Introduced by y-Ray Irradiation Under a 1,3-Butadiene Atmosphere", Colloid & Polymer Science, vol. 279, PDS. 754-762, 2001.
Oswald, P.R. at al., "Properties of Thermostable P-Glucosidase Immobilized Using Tris (Hydroxymethyl) Phosphine as a Highly Effective Coupling Agent", Enzyme and Microbial Technology, vol. 23, pos. 14-19, 1998.
Potezny, N. et al., "Urinary Oxalate Determination by Use of Immobilized Oxalate Oxidase in a Continuous-Flow System", Clinical Chemistry, vol. 29, pp. 16-20, Jan. 1983.
Pundir, C. et al., "Immobilization of Sorghum Leaf Oxalate Oxidase onto Alkylamine and Arylamine Glass", Chinese Journal of Biotechnology, vol. 15, pp. 129-138, 1999.
Reid, G. et al., "Microbial Adhesion and Biofilm Formation on Ureteral Stents in Vitro and in Vivo", Journal of Urology, vol. 148, pp. 1592-1594, Nov. 1992.
Robert, M. et al., "Double-J Ureteric Stent Encrustations: Clinical Study on Crystal Formation on Polyurethane Stents", Urologia Internationalis, vol. 58, pp. 100-104, 1997.
Santin, M. et al., "Effect of the Urine Conditioning Film on Ureteral Stent Encrustation and Characterization of its Protein Composition", Biomaterials, vol. 20, pp. 1245-1251, Jul. 1999.
Thakur, M. et al., "Discrete Analysis of Plasma Oxalate with Alkylamine Glass Bound Sorghum Oxalate Oxidase and Horseradish Peroxidase", Journal of Biochemical and Biophysical Methods, vol. 44, pp. 77-88, Jul. 2000.
Tieszer, C. et al., "XPS and SEM Detection of Surface Changes on 64 Ureteral Stents after Human Usage", J Biomed Materials Research, vol. 43, pp. 321-330, 1998.
Tieszer, C. et al., "Conditioning Film Depostion on Ureteral Stents After Implantation", Journal of Urology, vol. 160, pp. 876-881, Sep. 1998.
Tunney, M.M. et al., "Comparative Assessment of Ureteral Stent Biomaterial Encrustation", Biomaterials, vol. 17, pp. 1541-1547, Aug. 1996.
Urban, M.W. et al., "DMA and ATR FT-IR Studies of Gas Plasma Modified Silicone Elastomer Surfaces", Journal of Applied Polymer Science, vol. 39, pp. 265-283, 1990.
Wollin, T. et al., "Bacterial Biofilm Formation, Encrustation, and Antibiotic Adsorption to Ureteral Stents Indwelling in Humans", Journal of Endourology, vol. 12, pp. 101-111, Apr. 1998.
De Oliveria Neto, G. et al., "Oxalate Determination in Urine Using an Immobilized Enzyme on Sorghum Vulgare Seeds in a Flow Injection Conductimetric System", J. Braz. Chem. Soc., vol. 8, No. 1, pp. 47-51, 1997.
Barbalias, G. et al., "Encrustation of a Netal Alloy Urinary Stent: A Mechanistic Investigation", European Urology, Abstract, vol. 38, No. 2, pp. 1-2, 2000.
Sofer, M. et al., "Encrustation of Biomaterials in the Urinary Tract", Current Opinion in Urology, vol. 10, pp. 563-569, Nov. 2000.
International Search Report for related PCT Application No. PCT/US05/45457 dated Jun. 4, 2008.

(56) References Cited

OTHER PUBLICATIONS

Notice of Abandonment dated Dec. 12, 2011, for U.S. Appl. No. 11/659,583, filed Mar. 19, 2008 (Inventors—Sidhu et al.) (2 pages).
Non-Final Office Action dated May 23, 2011 for U.S. Appl. No. 11/659,583, filed Mar. 19, 2008 (Inventors—Sidhu et al.) (10 pages).
Yamanaka SA, et al. (1996) Enzymatic Activity of Oxalate Oxidase and Kinetic Measurements by Optical Methods in Transparent Sol-Gel Monoliths. J Sol-Gel Sci. 7: 117-121.
Non-Final Office Action dated Sep. 30, 2011 for U.S. Appl. No. 11/639,388, filed Dec. 14, 2006 (Inventors—Kaul et al.) (16 pages).
Kailasapathy, K. (2002) Microencapsulation of probiotic bacteria: Technology and potential applications. Curr Issues Intest Microbiol. 3:39-48.
Gombotz, W.R., et al. (1998) Protein release from alginate matrices. Adv Drug Deily Rev. 31(3): 267-285.
Non-Final Office Action dated Sep. 29, 2011 for U.S. Appl. No. 12/497,275, filed Jul. 2, 2009 (Inventors—Sidhu et al.) (10 pages).
Svedruzic, D. (2005) Mechanism of the reaction catalyzed by the oxalate decarboxylase from Bacillus subtilis. A dissertation for Ph.D at the University of Florida (pp. 1-122).
Extended European Search Report dated Feb. 9, 2009 for EP 08168165 filed on Nov. 3, 2008 and published as EP 2033651 on Mar. 11, 2009 (Applicant—OxThera, Inc. // Inventors—Allison et al.) (7 pages).
Hoppe B, et al. (2005) Oxalate degrading bacteria: new treatment option for patients with primary and secondary hyperoxaluria? Urol Res. 33(5): 372-375.
Siva S, et al. (2009) A critical analysis of the role of gut Oxalobacter formigenes in oxalate stone disease. BJU Int. 103(1): 18-21.
Khan M.Z.I., et al. (2000) A pH-dependent colon-targeted oral drug delivery system using methacrylic acid copolymers. II. Manipulation of drug release using Eudragit L100 and Eudragit S100 combinations. Drug Dev Ind Pharm. 26(5): 549-554.
Aoki, et al., "Purification of recombinant human pepsinogens and their application as immunoassay standards," Biochemistry and Molecular Biology International, 45(2):289-301 (1998).
Jin, et al., "The Solution and Solid State Stability and Excipient Compatibility of Parthenolide in Feverfew," AAPS PharmSciTech. 8(4): Article 105. El-E6 (2007).
Syedruzid, et al., "The enzymes of oxalate metabolism: unexpected structures and mechanisms," Archives of Biochemistry and Biophysics 433(1):176-192 (2005).
Abandonment dated Mar. 22, 2005 (U.S. Appl. No. 10/671,299).
Non-Final Rejection dated Sep. 14, 2004 (U.S. Appl. No. 10/671,299).
Abandonment dated Aug. 2, 2010 (U.S. Appl. No. 10/266,718).
Final Rejection dated Nov. 21, 2010 (U.S. Appl. No. 10/266,718).
Amendment/Request Reconsideration—After Non-Final Reject dated Nov. 9, 2009 (U.S. Appl. No. 10/266,718).
Non-Final Rejection dated Jul. 7, 2009 (U.S. Appl. No. 10/266,718).
Amendment Submitted/Entered with Filing of CPA/RCE dated Jun. 4, 2009 (U.S. Appl. No. 10/266,718.
Final Rejection dated Dec. 4, 2008 (U.S. Appl. No. 10/266,718).
Non-Final Rejection dated Feb. 15, 2008 (U.S. Appl. No. 10/266,718).
Non-Final Rejection dated Jul. 26, 2007 (U.S. Appl. No. 10/266,718).
Advisory Action (PTOL-303) dated Jan. 29, 2007 (U.S. Appl. No. 10/266,718).
Final Rejection dated Sep. 27, 2006 (U.S. Appl. No. 10/266,718).
Non-Final Rejection dated Mar. 28, 2006 (U.S. Appl. No. 10/266,718).
Requirement for Restriction/Election dated Dec. 5, 2005 (U.S. Appl. No. 10/266,718)
Requirement for Restriction / Election dated Jun. 29, 2005 (U.S. Appl. No. 10/266,718).
Final Rejection dated May 25, 2010 (U.S. Appl. No. 11/639,388).
Response after Non-Final Action dated Feb. 19, 2010 (U.S. Appl. No. 11/639,388).
Non-Final Rejection dated Oct. 22, 2009 (U.S. Appl. No. 11/639,388).
Requirement for Restriction / Election dated Aug. 7, 2009 (U.S. Appl. No. 11/639,388).

Request for Continued Examination (RCE) dated Jul. 13, 2010 (U.S. Appl. No. 11/640,126).
Final Rejection dated Apr. 14, 2010 (U.S. Appl. No. 11/640,126).
Response after Non-Final Action dated Jan. 15, 2010 (U.S. Appl. No. 11/640,126).
Non-Final Rejection dated Oct. 15, 2009 (U.S. Appl. No. 11/640,126).
Response to Election / Restriction dated Jul. 6, 2009 (U.S. Appl. No. 11/640,126).
Requirement for Restriction / Election dated Jun. 4, 2009 (U.S. Appl. No. 11/640,126).
Preliminary Amendment dated Jan. 3, 2007 (U.S. Appl. No. 11/640,126).
Extended European Search Report dated Sep. 14, 2009 issued in European App No. EP 09 164 430.2.
International Search Report and Wrritten Opinion for PCT Application No. PCT/US2005/016080 dated May 21, 2007.
Allison, M.J., H.M. Cook (1981) "Oxalate degradation by microbes of the large bowel of herbivores: the effect of dietary oxalate" Science 212:675-676.
Allison, Milton J. Karl A. Dawson William R. Mayberry, John G Foss (1985) "Oxalobacter fogrugons gen. ndv., sp. now.: oxalate-degracling anaerobes that inhibit the gastrointestinal tract" Arch Micro No1 141:1-7.
Allison, Milton J. Perbert M. Cook, David B. Millne, Sandra Gallagher, Ralph V. Clayman (1986) "Oxalate Degradalon by Gastrointestinal Bacteria from Humans" J.-Nutr. 116:455-460.
Allison Milton J., Steven L Daniel, Nqicy A. Comick (1995) "Oxalate-Degrading Bacteria" In: Khan, S.R. (ed), Calcium Oxalate in Biological Systems CRC F'ress, Chapter 7, pp. 1131468.
Bowerstock, T.L.L H. HogenEsch, M. Suckow, P. Guimond, S Martin, D. Borle, S. Torregrosa, H. Park,,K, Park (1999) "Oral vaccination of animals with antigens encapsulated in alginate microsphers" Vaccine 17:1804-1811.
Cho, Nam-Hyuk, S.-Y. Seong, K.-H. Chun, Y.-Fl. Kim. I.C. Kwon, B-Y, Atm, S.Y. Jeong (1998) Novel Mucosal immunization with polysaccharide-protein conjugates entrapped in microspheres, Journal or Controlled Release 53215-22.
Daniel,S.L.. P.A. Hartman, M.I. Allison (1993) "Intestinal Colonisation of laboratory Rats by Anaerobic Oxalate-degrading Bacteria: Effects on the Urinary and Faecal Excretion of Dietary Oxalate" Microbial Ecology in Health and Disease 6:277-283.
Daniel, Steven L, Paul A. Hartman, Milton .1. Allison (1987) "Microbial Degradation of Oxalate in the Gastrointestinal Tracts of Rats" Applied and Environmental Microbiology 53(8):1793-1797.
Dawson Karl A., Mi. Allison, P.A. Hartman (1980) "Isolation and Some Characteristics of Anaerobic Oxalate-begrading Bacteria from thc Rumen" Applied and Environmental Microbiology 40(4):833-839.
Doane, Uri T., Michael Liebrnan, Pallid R. Caldwell (1989) Microbial Oxalate Degradation: Effects on Oxalate and Calcium Balance in Humans: Nutrition Research 9:957-964.
Han et al., "The Relationship of Oxalobacter formigenes and Calcium Oxalate Calculi," Journal of Tongji Medical University, 15(4): 249-252, 1995.
Ito et al., (1995) "A New Oxalate-degrading Organism Isolated from Human Feces," Abstr. Annual Meeting Amer. Soc. Microbiol. Q-106.
Jensen, Neil S., Milton J. Allison (1994) "Studies on the Diversity Among Anaerobic oxalate Degrading Bacteria now in the Species oxalobacter formigenes" Abstr. General Meeting of the American Soc. Microbiol. 1-12.
Lung et al., (1991) "Cloning and expression of the oxalyl-CoA decarboxylase gene from the bacterium Oxalobacter formigenes: prospects for gene therapy to control Ca-oxalate kidney stone formation," American Journal of Kidney Disease vol. XVI(4): 381-385.
Sidhu et al., (1996) "Detection and Characterization of oxalobacter formigenes Strains Using oligonucleotide Probes," Meeting for Urolithaisis, pp. 537-539, pak, E.Y.C. et al., (ed.).
Xing et al., "Oral colon-specifc drug delivery for bee venom peptide: development of a coated calcium alginate gel bead-entrapped liposome," Journal of Controlled Release, vol. 93, pp. 293-300, 2003.

(56) References Cited

OTHER PUBLICATIONS

Bodemeier et al., "A Novel Approach to the Oral Delivery of Micro- or Nanoparticles," Pharmaceutical Research, vol. 6, No. 5, pp. 413-417, 1989.
Leslie et al., Trehalose and Sucrose Protect Both Membranes and Proteins in Intact Bacteria during Drying, Applied and Environmental Microbiology, vol. 61, No. 10, pp. 3592-3597, Oct. 1995.
Lane, Oxalate, germin, and the extracellular matrix of higher plants, FASEB J., vol. 8, pp. 294-301, 1994.
Dominguez-Munoz et al., "Effect of oral pancreatic enzyme administration on disgestive function in healthy subjects: comparison between two enzyme preparations," Aliment Pharmacol. Ther., vol. 11, pp. 403-408, 1997.
Baetz et al., "Purification and Characterization of Formyl-Coenzyme A Transferase from Oxalobacter formigenes," Journal of Bacteriology, vol. 172, No. 7, pp. 3537-3540, 1990.
Baetz et al., "Purification and Characterization of Oxalyl-Coenzyme A Decarboxylase from Oxalobacer formigenes," Journal of Bacteriology, vol. 171, No. 5, 1989.
Office Action dated Mar. 31, 2005 in U.S. Appl. No. 10/868,242 (U.S. Pat. No. 8,486,389).
Office Action dated Nov. 18, 2005 in U.S. Appl. No. 10/868,242 (U.S. Pat. No. 8,486,389).
Office Action dated Sep. 21, 2006 in U.S. Appl. No. 10/868,242 (U.S. Pat. No. 8,486,389).
Office Action dated Sep. 5, 2007 in U.S. Appl. No. 10/868,242 (U.S. Pat. No. 8,486,389).
Office Action dated Apr. 10, 2008 in U.S. Appl. No. 10/868,242 (U.S. Pat. No. 8,486,389).
Office Action dated Feb. 19, 2009 in U.S. Appl. No. 10/868,242 (U.S. Pat. No. 8,486,389).
Office Action dated Dec. 10, 2009 in U.S. Appl. No. 10/868,242 (U.S. Pat. No. 8,486,389).
Office Action dated Sep. 17, 2010 in U.S. Appl. No. 10/868,242 (U.S. Pat. No. 8,486,389).
Office Action dated Jun. 10, 2011 in U.S. Appl. No. 10/868,242 (U.S. Pat. No. 8,486,389).
Office Action dated Oct. 16, 2012 in U.S. Appl. No. 10/868,242 (U.S. Pat. No. 8,486,389).
Notice of Allowance dated Mar. 20, 2013 in U.S. Appl. No. 10/868,242 (U.S. Pat. No. 8,486,389).
Office Action dated Apr. 2, 2014 in U.S. Appl. No. 11/640,126 (US 2007/0184118).
Office Action dated Oct. 7, 2013 in U.S. Appl. No. 11/640,126 (US 2007/0184118).
Office Action dated Jan. 31, 2014 in U.S. Appl. No. 13/851,594 (2013/0216515).
Holmes et al., "Contribution of dietary oxalate to urinary oxalate excretion," Kidney International, vol. 59, pp. 270-276, 2001.
Milliner, "Treatment of the primary hyperoxalurias: A new chapter," Kidney International, vol. 70, pp. 1198-1200, 2006.
Hatch et al., "Oxalobacter sp. reduces urinary oxalate excretion by promoting enteric oxalate secretion," Kidney International, vol. 69, pp. 691-698, 2006.
Hoppe et al., "Oxalobacter formigenes: a potential tool for the treatment of primary hyperoxaluria type 1," Kidney International, vol. 70, pp. 1305-1311, 2006.
Duncan et al., "Oxalobacter formigenes and its Potential Role in Human Health," Applied and Environmental Microbiology, vol. 68, No. 8, pp. 3841-3847, Aug. 2002.
Partial European Search Report issued in application No. EP 14 18 0734 dated Oct. 14, 2014.
Notice of Allowance dated Jul. 30, 2014 in U.S. Appl. No. 11/640,126 (US 2007/0184118).
Notice of Allowance dated Sep. 22, 2014 in U.S. Appl. No. 13/851,594 (US 2013/0216515).
Office Action dated May 23, 2014 in U.S. Appl. No. 13/851,594 (US 2013/0216515).
European Search Report dated Jan. 21, 2015 in application No. EP 14 18 0734.
Daniel et al.,"Intestinal Colonization of Laboratory Rats with Oxalobacter formigenes," Applied and Environmental Microbiology, vol. 53, No. 12, pp. 2767-2770, Dec. 1987.

\* cited by examiner

FIG. 4

| Table-1:EFFECT OF *O.FORMIGENES* SUPPLEMENTATION (IxOC-3 FORMULATION) ON URINARY OXALATE EXCRETION (MICROMOLES/DAY) IN RATS FED HIGH OXALATE DIET | | | | | |
|---|---|---|---|---|---|
| GROUP NO. | Day -1 | Day 7 | Day 14 | Day 21 | Day 28 |
| I (Placebo) | 4.57 ± 0.82 | 13.97 ± 3.32 | 17.56± 6.24 | 22.75 ± 3.16 | 25.43 ± 8.04 |
| II (Low Dose) | 4.16 ± 0.58 | 11.43 ± 1.78 | 12.82± 4.21 | 13.00 ± 2.11$^a$ | 13.63 ± 2.53$^b$ |
| IIII(High Dose) | 4.04 ±1.27 | 14.22 ± 3.00 | 12.74 ± 2.69 | 13.60 ± 3.29$^a$ | 14.57 ± 4.64$^c$ |
| Group I = 1% oxalate (HOD)+ 0 cfu | | | $^a$ $p<0.0001$ as compared to Group-I | | |
| Group II = HOD + 10$^6$ cfu *O.formigenes* | | | $^b$ $p=0.0022$ as compared to Group-I | | |
| Group III = HOD + 10$^7$ cfu *O.formigenes* | | | $^c$ $p=0.0041$ as compared to Group-I | | |

COMPOSITIONS AND METHODS FOR TREATING OR PREVENTING OXALATE-RELATED DISEASE

CROSS-REFERENCE TO A RELATED APPLICATION

This application is a continuation of U.S. patent application Ser. No. 10/868,242, filed Jun. 15, 2004 (now U.S. Pat. No. 8,486,389, issued Jul. 16, 2013), the contents of which are hereby incorporated by reference in thier entirety.

FIELD OF THE INVENTION

The present invention relates to compositions and methods for treating and preventing oxalate related conditions. More particularly, the invention relates to compositions and methods comprising oxalate-degrading or oxalate-reducing bacteria and enzymes.

BACKGROUND

Kidney-urinary tract stone disease (urolithiasis) is a major health problem throughout the world. Most of the stones associated with urolithiasis are composed of calcium oxalate alone or calcium oxalate plus calcium phosphate. Other disease states have also been associated with excess oxalate. These include, vulvodynia, oxalosis associated with end-stage renal disease, cardiac conductance disorders, Crohn's disease, and other enteric disease states.

Oxalic acid, and/or its salt, oxalate, is found in a wide variety of foods, and is therefore, a component of many constituents in human and animal diets. Increased oxalate absorption may occur after foods containing elevated amounts of oxalic acid are eaten. Foods such as spinach and rhubarb are well known to contain high amounts of oxalate, but a multitude of other foods and beverages also contain oxalate. Because oxalate is found in such a wide variety of foods, diets that are low in oxalate and which are also palatable are hard to formulate. In addition, compliance with a low oxalate diet is often problematic.

Endogenous oxalate is also produced metabolically by normal tissue enzymes. Oxalate, which includes dietary oxalate that is absorbed as well as oxalate that is produced metabolically, is not further metabolized by tissue enzymes and must therefore be excreted. This excretion occurs mainly via the kidneys. The concentration of oxalate in kidney fluids is critical, with increased oxalate concentrations causing increased risk for the formation of calcium oxalate crystals and thus the subsequent formation of kidney stones.

The risk for formation of kidney stones revolves around a number of factors that are not yet completely understood. Kidney or urinary tract stone disease occurs in as many as 12% of the population in Western countries and about 70% of these stones are composed of calcium oxalate or of calcium oxalate plus calcium phosphate. Some individuals (e.g., patients with intestinal disease such as Crohn's disease, inflammatory bowel disease, or steatorrhea and also patients that have undergone jejunoileal bypass surgery) absorb more of the oxalate in their diets than do others. For these individuals, the incidence of oxalate urolithiasis increases markedly. The increased disease incidence is due to increased levels of oxalate in kidneys and urine, and this, the most common hyperoxaluric syndrome in man, is known as enteric hyperoxaluria. Oxalate is also a problem in patients with end-stage renal disease and there is recent evidence (Solomons, C. C., M. H. Melmed, S. M. Heitler [1991] "Calcium citrate for vulvar vestibulitis" *Journal of Reproductive Medicine* 36:879-882) that elevated urinary oxalate is also involved in vulvar vestibulitis (vulvodynia).

Bacteria that degrade oxalate have been isolated from human feces (Allison, M. J., H. M. Cook, D. B. Milne, S. Gallagher, R. V. Clayman [1986] "Oxalate degradation by gastrointestinal bacteria from humans" *J. Nutr.* 116:455-460). These bacteria were found to be similar to oxalate-reducing bacteria that had been isolated from the intestinal contents of a number of species of animals (Dawson, K. A., M. J. Allison, P. A. Hartman [1980] "Isolation and some characteristics of anaerobic oxalate-degrading bacteria the rumen" *Appl. Environ. Microbiol.* 40:833-839; Allison, M. J., H. M. Cook [1981] "Oxalate degradation by microbes of the large bowel of herbivores: the effect of dietary oxalate" *Science* 212:675-676; Daniel, S. L., P. A. Hartman, M. J. Allison [1987] "Microbial degradation of oxalate in the gastrointestinal tracts of rats" *Appl. Environ. Microbiol.* 53:1793-1797). These bacteria are different from any previously described organism and have been given both a new species and a new genus name (Allison, M. J., K. A. Dawson, W. R. Mayberry, J. G. Foss [1985] *"Oxalabacter formigenes* gen. nov., sp. nov.: oxalate-degrading anaerobes that inhabit the gastrointestinal tract" *Arch. Microbiol.* 141: 1-7).

Not all humans carry populations of *O. formigenes* in their intestinal tracts (Allison, M. J., S. L. Daniel, N. A. Comick [1995] "Oxalate-degrading bacteria" In Khan, S. R. (ed.), *Calcium Oxalate in Biological Systems* CRC Press; Doane, L. T., M. Liebman, D. R. Caldwell [1989] "Microbial oxalate degradation: effects on oxalate and calcium balance in humans" *Nutrition Research* 9:957-964). There are low concentrations or a complete lack of oxalate degrading bacteria in the fecal samples of persons who have had jejunoileal bypass surgery (Allison et al. [1986] "Oxalate degradation by gastrointestinal bacteria from humans" *J. Nutr.* 116:455-460). Also, certain humans and animals may maintain colonies of *O. formigenes* but nevertheless have excess levels of oxalate for reasons which are not clearly understood.

What is needed are methods for treating humans and animals to reduce the oxalate levels in their bodies so that oxalate-related conditions are treated or prevented. Desirable methods would include administration of oxalate-reducing compositions.

BRIEF SUMMARY OF THE INVENTION

The present invention comprises compositions and methods for treating and preventing, oxalate-related conditions. Compositions of the present invention comprise among others, microorganisms that can reduce oxalate and compositions that comprise enzymes that reduce oxalate. Methods of the present invention comprise administering the compositions to treat or prevent oxalate-related conditions. One embodiment comprises methods which reduce the risk for developing oxalate-related disorders by reducing the amount of oxalate in the intestinal tract. This reduction in the intestinal tract leads to a reduction in systemic oxalate levels thereby promoting good health.

In one embodiment of the subject invention, a reduction in oxalate absorption is achieved by supplying oxalate-degrading bacteria to the intestinal tract. In a preferred embodiment, these bacteria are *Oxalobacter formigenes*. These bacteria use oxalate as a growth substrate. This utilization reduces the concentration of soluble oxalate in the intestine and, thus, the amount of oxalate available for absorption. A reduction of oxalate in the intestinal tract can also lead to removal of oxalate from the circulatory system. Methods of the present invention contemplate an overall reduction of the oxalate load in an individual.

In a specific embodiment, the subject invention provides methods and compositions for the delivery of *O. formigenes* to the intestinal tracts of persons who are at increased risk for oxalate-related disease. These bacteria and their progeny replicate in the intestine and remove oxalate from the intestinal tract, thereby reducing the amount of oxalate available for absorption and leading to increased oxalate excretion from the blood into the intestine.

In accordance with the teaching of the subject invention, oxalate-degrading microbes other than *O. formigenes* which utilize oxalate as a substrate can also be used to achieve therapeutic oxalate degradation thereby reducing the risk of urolithiasis and other oxalate-related disorders. Such other microbes may be, for example, bacteria such as clostridia or pseudomonads. Additionally, the present invention comprises methods and compositions for providing exogenous polynucleotides capable of conferring oxalate-reducing function to microorganisms that can be used to transform nave microorganisms, those originally unable to reduce oxalate, into microorganisms capable of reducing oxalate.

In one embodiment of the subject invention, compositions comprise the microbes that are used to degrade oxalate produce enzymes which confer upon these microbes the ability to degrade oxalate. In an alternative embodiment, the compositions may comprise microbes that are transformed with polynucleotide sequences which confer upon the transformed microbes the ability to degrade oxalate. Polynucleotide sequences that encode oxalate-reducing genes are contemplated by the present invention. Polynucleotide sequences coding for enzymes found in oxalate-reducing microorganisms, such as bacteria or fungi, or other oxalate-reducing enzymes can be used in the methods of the present invention. Polynucleotides may be used to transform cells so that the cells have more oxalate-reduction activity, the same oxalate-reduction activity, or less oxalate-reduction activity than naturally occurring oxalate reducing microorganisms. Polynucloetides may also be used in synthetic or ex vivo systems to provide proteins having oxalate reducing activity.

The enzymes formyl-CoA transferase and oxalyl-CoA decarboxylase have been identified as playing a role in oxalate degradation. Enzymes used in the methods and compositions of the present invention include, but are not limited to formyl-CoA transferase, oxalyl-CoA decarboxylase, oxalate oxidase, oxalate decarboxylase and other enzymes, cofactors, and co-enzymes that are substituents of oxalate degradation pathways or involved in oxalate metabolic pathways, particularly oxalate reduction.

In one embodiment of the subject invention, an appropriate host can be transformed with exogenous polynucleotides encoding these enzyme or enzyme related activities thereby conferring upon the transformed host the ability to augment oxalate degradation. The host may be, for example, a microbe which is particularly well adapted for oral administration and/or colonizing the intestines. Alternatively, the host may be a plant which, once transformed, will produce the desired enzyme activities thereby making these activities available in the intestine when the plant material is consumed. Alternatively, the transformed plant may have a lower amount of oxalate, optionally due to the actions of the proteins provided by the transformation, and thus when consumed, the plant will not provide as much oxalate to the diet as would a nontransformed plant.

The present invention also comprises methods and compositions for plants transformed with oxalate-degrading or oxalate-reducing enzymes wherein these plants have enhanced resistance to fungi which require oxalate for their pathogenesis of plants or which produce oxalic acid as a mechanism for their pathogenesis of plants.

The present invention also comprises methods and compositions comprising enzymes for reducing oxalate levels in order to treat or prevent oxalate related conditions. For example, a reduction in oxalate levels is achieved by administering enzymes which act to degrade oxalate. These enzymes may be isolated and purified or they may be administered as a cell lysate. The cell lysate may be made from any microorganism that has oxalate-reducing functions, for example, *O. formigenes*. In a specific embodiment, the enzymes which are administered are one or more of the enzymes of the present invention such as, but not limited to, oxalate decarboxylase, oxalate oxidase, formyl-CoA transferase and oxalyl-CoA decarboxylase. Optionally, additional factors which improve enzyme activity can be administered. These additional factors may be, for example, oxalyl CoA, $MgCl_2$, and TPP (thiamine diphosphate, an active form of vitamin $B_1$). The compositions comprising enzymes comprise one or more enzymes, and optionally, cofactors, coenzymes, and other agents that enhance enzyme activity, individually or in combination.

In one embodiment of the subject invention, a reduction in oxalate levels is achieved by administering oxalate-degrading enzymes produced by a recombinant microbe, such as *Escherichia coli* which has been transformed to express oxalate-degrading enzymes. The recombinant host may be administered in either a viable or non-viable form. A further aspect of the subject invention pertains to pharmaceutical compositions and/or nutritional supplements for oral administration. These compositions release the oxalate degrading microbes, or oxalate degrading enzymes, in the intestines of humans or animals. The compositions of the present invention comprise pharmaceutically acceptable formulations. For example, the methods and compositions of the present invention comprise a dose delivery system that provides the compositions to the desired locations, such as delivery of the compositions to the intestines of the recipient. The compositions of the present invention may be administered as a constituent of foods, such as milk, meats, and yogurt.

In a further embodiment of the subject invention, a reduction in oxalate absorption is achieved in domesticated, agricultural, or exotic animals deficient in oxalate-degrading bacteria by administering oxalate-degrading microorganisms, plants, and enzymes individually or in combinations Methods of the present invention comprise treating or preventing oxalate-related conditions in humans and animals by administering an effective amount of oxalate reducing compositions comprising one or more oxalate reducing microorganisms, one or more oxalate reducing enzymes or combination and mixtures thereof. Oxalate-related conditions include, but are not limited to, hyperoxaluria, primary hyperoxaluria, idiopathic calcium oxalate kidney stone disease (urolithiasis), enteric hyperoxaluria, vulvodynia, oxalosis associated with end-stage renal disease, cardiac conductance disorders, inflammatory bowel disease, Crohn's disease and ulcerative colitis.

BRIEF DESCRIPTION OF THE FIGURES

FIG. 4 a graph of excreted oxalate.

DETAILED DISCLOSURE OF THE INVENTION

Figure 1A:
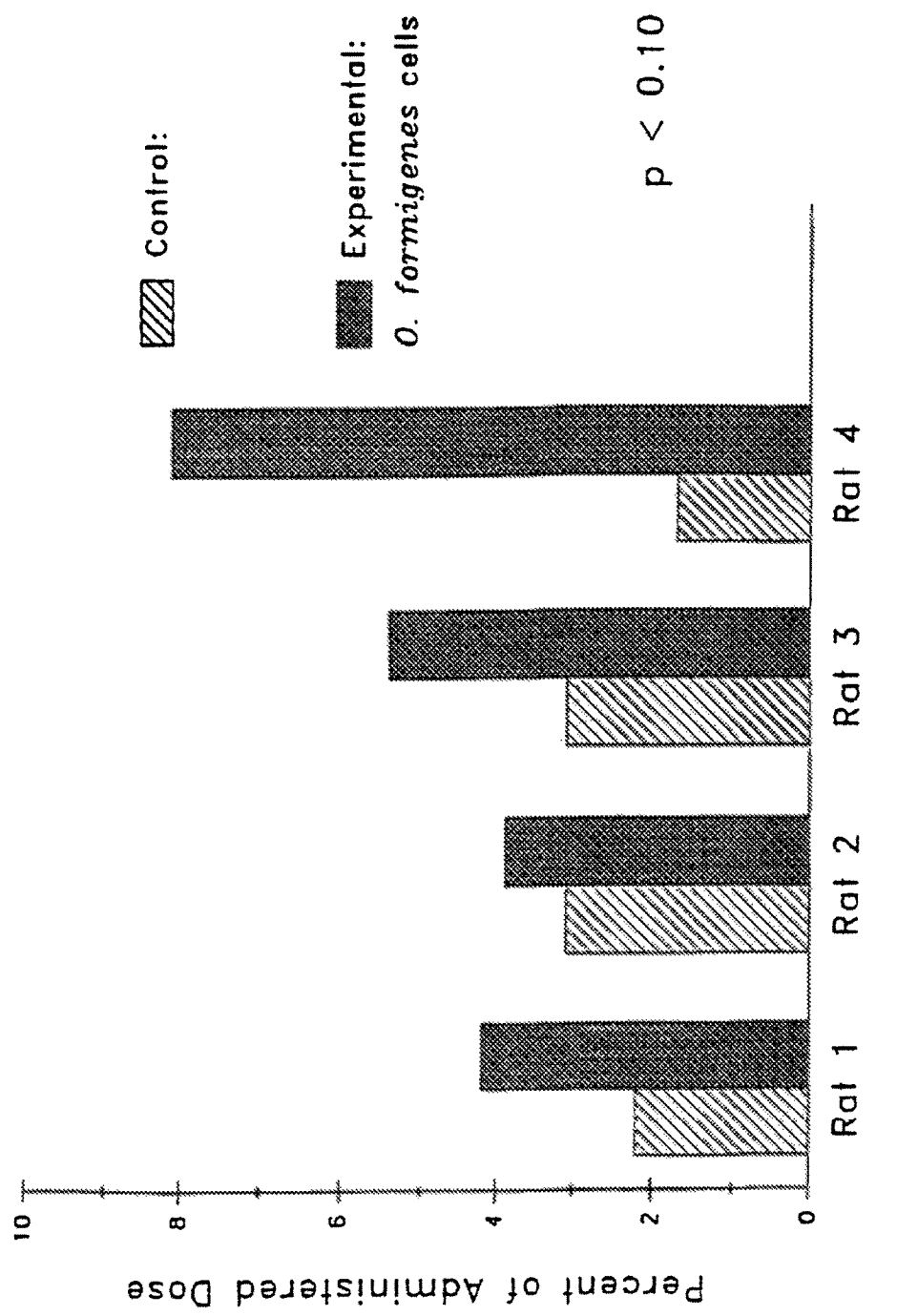
FIG. 1A is a graph of data from a high calcium diet.

The present invention comprises methods and compositions for oxalate reduction. The compositions of the present invention comprise microorganisms, enzymes, polynucleotide sequences, vectors, cells, plants and animals that are capable of reducing oxalate. Compositions comprise microorganisms that are capable of reducing oxalate. Such microorganisms include, but are not limited to *Oxalobacter formigenes, Pseudomonas, Clostridia, Lactobacilli, Bifidobacteria*, some or all of which are capable of reducing oxalate, but also include microorganisms, such as bacteria or fungi that are transformed with exogenous polynucleotides so that oxalate reducing ability is conferred. Additionally, the microorganisms of the present invention include microorganisms that have been transformed with one or more oxalate-reducing vectors comprising endogeneous or exogeneous polynucleotide sequences that code for oxalate-reducing enzymes or associated activities such that the microorganisms are "super reducers". Super reducers have enhanced native oxalate reducing abilities, for example, in transformation of *Oxalobactor formigenes* with additional oxalate reducing sequences, or microorganisms that do not originally have oxalate reducing activity that are transformed with one or more sequences coding for oxalate reducing peptides resulting in enhanced oxalate reducing activity. The oxalate reducing activity encoding sequences may or may not intercalate into the genome or other vectors found in the microorganism. Such transformation may include provision of gene sequences that code for oxalate reducing proteins or peptides or may provide blocking nucleotides such as antisense or iRNA.

Compositions also comprise enzymes that are components of oxalate reduction pathways. Such compositions comprise one or more enzymes and optionally include cofactors, coenzymes, and other factors needed or desired for enzyme activity. Compositions comprise one or more enzymes including, but not limited to, oxalate reducing enzymes and other enzymes involved in oxalate metabolism found in plants, animals or humans. The compositions comprise one or more of the oxalate reducing enzymes taught herein. As used herein, the term "one or more enzymes" means that one enzyme, such as formyl-CoA transferase is intended, or that more than one enzyme, for example formyl-CoA transferase and oxalate decarboxylase is intended. As is known in the art, the term does not mean one enzyme molecule, but multiples of molecules of one or more enzyme types.

As used herein, the terms oxalate-degrading enzymes and oxalate-reducing enzymes are interchangeable and both refer to enzymes involved in the reduction or degradation of oxalate in any organism, or to active fragments or recombinant proteins comprising active fragments capable of reducing or degrading oxalate.

Enzyme compositions of the present invention may also comprise formulations that provide protection of the active enzyme molecules from degradation by the stomach or intestinal environment. For example, compositions of enzymes comprise compositions that can protect or cage the enzymes. The enzymes may be covalently linked to other compounds, including but not limited to PEG. The enzyme may be caged or entrapped within a structure such as inside a three dimensional mesh structure, for example, made from polymers that either degrade to release the enzymes or that have pore sizes that allow either the enzyme to leave the structure or the substrates to penetrate the structure to reach the enzymes. For example, the pore size would allow low molecular weight oxalate and formate to diffuse to the area where the enzymes are present. Additionally, the enzymes may or may not be covalently attached to the polymer structure. Methods and devices for protecting active enzymes from degradation in proteolytic or other environments harmful to enzymes.

The compositions of the present invention also comprise polynucleotide sequences that encode peptides or proteins that are involved in oxalate reduction pathways. Such polynucleotide sequences can be derived from any source and can be used in methods known to those skilled in the art, such as for transformation of cells of microbial, plant or animal origin, and including whole organisms.

Compositions of the present invention also include plants and animals that have altered oxalate reduction function. For example, such plants include plants that have been transformed by polynucleotide compositions so that the amount of oxalate in the plant is lowered or the amount of oxalic acid produced is increased when compared to untransformed plants. Compositions of the present invention also comprise animals that have an enhanced ability to reduce oxalate. For example, animals having enhanced oxalate reduction abilities can be used as in vivo models for studying oxalate related conditions.

Methods of the present invention comprise making and using the compositions of the present invention. Methods of the present invention comprise transforming cells, plants and animals by methods known to those skilled in the art for the introduction of exogenous polynucleotide sequences. Such polynucleotide sequences can be derived from any source and can be used in methods known to those skilled in the art, such as for transformation of cells of microbial, plant or animal origin, and including whole organisms. Methods also comprise making compositions comprising cell lysates having oxalate reducing activity, compositions comprising one or enzymes having oxalate reducing activity, and compositions comprising dietary constituents made from plants or microorganisms having altered oxalate levels.

Methods of the present invention comprise using the compositions of the present invention. Such uses include providing polynucleotide sequences to cells to enhance or repress the oxalate reducing ability of the cells. The present invention comprises methods of administering the compositions of the present invention to plants or animals for altering the oxalate levels of the plant or animal. Methods also include dietary supplementation methods such that the compositions of the present invention are administered to plants or animals in food or fertilizer sources or concurrent with food or fertilizer sources to alter the oxalate levels in the food, during the digestion of the food or during the uptake by the plants.

Methods of the present invention comprise methods of treating or preventing oxalate related conditions. Methods comprise administering the compositions of the present invention in amounts effective to alter the oxalate level in an organism. Such methods are effective for treatment of oxalate conditions in humans and animals including, but not limited to, hyperoxaluria, primary hyperoxaluria, idiopathic calcium oxalate kidney stone disease (urolithiasis), enteric hyperoxaluria, vulvodynia, oxalosis associated with end-stage renal disease, cardiac conductance disorders, inflammatory bowel disease, Crohn's disease and ulcerative colitis.

The subject invention pertains to the introduction of compositions comprising one or more oxalate-degrading bacteria and/or enzymes into a human or animal intestinal tract where the activity of the compositions reduces the amount and/or concentration of oxalate present thereby reducing the risk of disease due to oxalate.

The present invention comprises methods and compositions for the treatment and prevention of oxalate-related conditions in humans and animals. A method for treating oxalate conditions comprises administering a composition comprising one or more oxalate-reducing enzymes. Such compositions may be administered one or more times a day for one or more days depending on the severity of the oxalate-related condition or the amount of oxalate in the gut or body fluids of the human or animal. The treatments may continue as long as unwanted levels or oxalate are present in the human or animal. For example, the enzyme composition may be administered one or more times a day for a range of time including from one day to years. For humans or animals with chronic oxalate-related conditions, the composition may be administered for the entire remaining lifespan of the human or animal.

The methods for treating and preventing oxalate-related conditions comprise administering a composition comprising an effective amount of oxalate-reducing enzymes. The amount of enzyme in the composition comprises an amount of activity units of oxalate-reducing enzyme activity that will reduce a portion of the oxalate present in the intestines of the individual or a level of activity units of oxalate-reducing enzyme activity that will initiate a reduction in the amount of oxalate or maintain a lowered amount of oxalate in the individual compared to the amount of oxalate present before administration of the composition. The number of activity units of oxalate-reducing enzyme activity that can be used in a single dose composition can range from about 0.0001 units to about 5,000 units, from about 5 units to 100 units, and all ranges encompassed therein. The compositions may further include other enzymes, cofactors, substrates, coenzymes, minerals and other agents that are helpful in the reduction of oxalate. An unit of the enzyme is the amount of enzyme that will degrade one micromole of oxalate per minute at 37 C.

In a specific embodiment, the subject invention pertains to methods for the preparation and administration of compositions comprising cells of oxalate-degrading bacteria of the species, *Oxalobacter formigenes*, to the human or animal intestinal tract where the activity of the microbes reduces the amount of oxalate present in the intestine thereby causing a reduction of concentrations of oxalate in the kidneys and in other cellular fluids. In another embodiment, the present invention comprises methods for the preparation and administration of compositions comprising one or more oxalate-degrading enzymes, derived from any source, to the human or animal intestinal tract where the activity of the one or more enzymes reduces the amount of oxalate present in the intestine and lead to a reduction of concentrations of oxalate in the kidneys and in other cellular fluids. The introduced cells or enzymes degrade oxalate and the bacteria may or may not replicate in the intestinal habitat so that progeny of the initial cells colonize the intestine and continue to remove oxalate. The presence of oxalate reducing bacteria or oxalate reducing bacteria reduces the risk for formation of kidney stones as well as other disease complications caused by oxalic acid. In a preferred embodiment for human use, the specific strains of *O. formigenes* used are strains isolated from human intestinal samples. The strains are thus part of the normal human intestinal bacterial flora. However, since they are not present in all persons, or are present in insufficient numbers, the introduction of these organisms corrects a deficiency that exists in some humans.

Though not wishing to be bound by any particular theory, it is believed that enrichment of the contents of the intestines with one or more species of oxalate-degrading bacteria or oxalate reducing enzymes causes a reduction of oxalate in the intestinal contents. Some of the bacteria or administered enzymes carry out oxalate degradation at or near the site of absorption. The activity of the bacteria or administered enzymes decrease the level of absorption of dietary oxalate. A reduction in oxalate concentration in the intestines can also lead to a removal of oxalate from cells and the general circulation. More specifically, a reduction of oxalate concentration in the intestines can also lead to enhanced secretion of oxalate into the intestine from the blood and thus reduce the amount of oxalate that needs to be excreted in urine. Thus, the methods of the subject invention for administering oxalate reducing bacteria or oxalate reducing enzymes can be used to treat or prevent oxalte-related conditions such as primary hyperoxaluria in addition to treatment of dietary hyperoxaluria. The compositions and methods of the subject invention are particularly advantageous in the promotion of healthy oxalate levels in humans and animals.

Pharmaceutical and nutriceutical compositions for the introduction of oxalate degrading bacteria or one or more oxalate degrading enzymes, alone or in combinations, into the intestine include bacteria or enzymes that have been lyophilized or frozen in liquid or paste form and encapsulated in a gel capsule or other enteric protection. The gel cap material is preferably a polymeric material which forms a delivery pill or capsule that is resistant to degradation by the gastric acidity and enzymes of the stomach but is degraded with concomitant release of oxalate-degrading compositions by the higher pH and bile acid contents in the intestine. The released composition then converts oxalate present in the intestine to harmless products. Pharmaceutical or nutriceutical carriers also can be combined with the bacteria or enzymes. These would include, for example, saline-phosphate buffer. Methods of the present invention comprise administration of oxalate-reducing compositions to the intestinal tract of humans or animals.

Oxalate-reducing compositions comprising one or more oxalate reducing bacteria or one or more oxalate reducing enzymes, or combinations of bacteria and enzymes, to be administered can be delivered as capsules or microcapsules designed to protect the composition from adverse effects of acid stomach. One or more of several enteric protective coating methods can be used. Descriptions of such enteric coatings include the use of cellulose acetate phthalate (CAP) (Yacobi, A., E. H. Walega, 1988, Oral sustained release formulations: Dosing and evaluation, Pergammon Press). Other descriptions of encapsulation technology include U.S. Pat. No. 5,286,495, which is incorporated herein by reference. The compositions of the subject invention can also be formulated as suppositories.

Other methods of administration of these compositions comprising one or more microorganisms, one or more oxalate reducing enzymes or combinations and mixtures, to the intestines include adding the compositions directly to food sources. The one or more bacteria may be added as freshly harvested cells, freeze dried cells, or otherwise protected cells. The one or more enzymes may be added as lyophilized proteins, encapsulated or microencapsulated enzyme compositions, enzymes complexed to other materials to maintain activity of the enzymes, and other methods known to those skilled in the art for adding active enzymes to compositions. Foods may be supplemented with oxalate degrading compositions without affecting their taste or appearance. These foods may be, for example, yogurt, milk, peanut butter or chocolate. Upon ingestion, when the food products are being digested and absorbed by the intestines, the oxalate degrading compositions, including one or more microorganisms, one or more enzymes or combinations, degrade oxalate present in the intestines thus reducing absorption of oxalate into the bloodstream.

As noted above, a variety of foods can be supplemented with oxalate degrading compositions. Methods for making such foods containing oxalate reducing compositions include admixing a food material with an oxalate reducing composition. For example, oxalate reducing microbes can be grown in media and separated from the media by, for example, centrifugation. Traditional yogurt cultures obtained from a commercial dairy can be mixed with the oxalate degrading microbial culture. This mixture of cultures then can be added to the basic dairy yogurt premix without adversely affecting taste or consistency. The yogurt can then be produced and packaged using traditional commercial procedures. In another example, the oxalate degrading bacteria can be added to already produced yogurts. In a similar method, an oxalate reducing composition comprising one or more oxalate reducing enzymes can be added to the yogurt bacterial culture or to the yogurt food product.

Another example of the methods of the present invention is to add the oxalate reducing composition to milk after it has been homogenized and sterilized. Such a method is currently used in the dairy industry for adding *Lactobacillus acidophilis* organisms to milk. Any food source containing bacteria can be used by supplementing with oxalate-degrading bacteria. These food products include cheese or meat products that have desirable microorganisms added during processing. Foods comprising oxalate reducing compositions comprising oxalate reducing enzymes are not limited to those foods that comprise microorganisms, but include any food source in which active enzymes can be added. The materials commonly thought of as food materials can be used as carrier material for the enzymes so that the enzymes are active on oxalate present in the food material at any stage of production or growth of the food material, or any stage of or digestion by the human or animal, or on oxalate present in the gut.

In yet a further embodiment, the subject invention provides a novel enzyme delivery system. This system comprises a plant which has been transformed with heterologous polynucleotide(s) to express oxalate-degrading enzymes. The enzyme-expressing transgenic plant may be administered to patients as a constituent of a salad, for example. Further, the enzyme-expressing plant may be administered to animals as a constituent of feed, for example, or grown in grazing pasture. The animals to which these products may be fed include, for example, cattle, pigs, dogs and cats.

Thus, as an alternative method of administration to the intestine, plants are genetically engineered to express oxalate-degrading enzymes. These transgenic plants are added to the diet, with the activity of the enzymes causing a decrease in the presence of oxalate. DNA sequences encoding these enzymes are known to those skilled in the art and are described in, for example, WO 98/16632.

In addition to plants which can be used as a dietary component to promote healthy oxalate levels in humans or animals, the subject invention provides plants with enhanced resistance to microbial infections. Specifically, the transformed plants of the subject invention are protected against microbes which require or use the presence of oxalate for plant pathogenicity. The plants of the subject invention, which are transformed to express oxalate-degrading enzymes are protected against, for example, certain fungi which need oxalate for pathogenicity. The genes encoding the enzymes can be modified to enhance expression and/or stability in plants. Also, the expression may be under the control of promoters which direct expression in particular tissues.

In one embodiment, the strains of bacteria, for example, *O. formigenes*, used according to the subject invention are pure cultures that are isolated from anaerobic cultures that have been inoculated with dilutions of intestinal contents from normal humans or, for use with animals, from normal animals. A special calcium oxalate containing medium that allows detection of oxalate degrading colonies can be used. In one embodiment, the purity of each strain can be assured through the use of at least two subsequent repetitive cloning steps.

Strains of *O. formigenes* useful according to the subject invention have been characterized based upon several tests, these include: patterns of cellular fatty acids, patterns of cellular proteins, DNA and RNA (Jensen, N. S., M. J. Allison (1995) "Studies on the diversity among anaerobic oxalate degrading bacteria now in the species *Oxalobacter formigenes*" Abstr. to the General Meeting of the Amer. Soc. Microbiol., 1-29), and responses to oligonucleotide probes (Sidhu et al. 1996). Two groups of these bacteria (Groups I and II, both existing within the present description of the species) have been described. Strains used have been selected based upon oxalate degrading capacity, and evidence of the ability to colonize the human intestinal tract. Strains selected include representatives of both Groups I and II of the species.

One embodiment of the present invention involves procedures for selection, preparation and administration of the appropriate oxalate-degrading bacteria to a diversity of subjects. Prominently, but not exclusively, these are persons or animals which do not harbor these bacteria in their intestines. These non-colonized or weakly-colonized persons or animals are identified using tests that allow for rapid and definitive detecting of *O. formigenes* even when the organisms are at relatively low concentrations in mixed bacterial populations such as are found in intestinal contents. The methods of the subject invention can also be used to treat individuals or animals whose oxalate-degrading bacteria have been depleted due to, for example, antibiotic treatment or in post-operative situations. The methods of the subject invention can also be used to treat individuals or animals who have colonies of oxalate-degrading bacteria but who still have unhealthy levels of oxalate due to, for example, oxalate susceptibility and/or excessive production of endogenous oxalate.

Bacteria which can be used according to the subject invention can be identified by at least two methods:

1) Oligonucleotide probes specific for these bacteria can be used; and/or

2) A culture test wherein an anaerobic medium with 10 mM oxalate is inoculated and after incubation at 37.degree. C. for 1 to 7 days, the loss of oxalate is determined.

Pure cultures of *O. formigenes* strains can be grown in large fermenter batch cultures and cells can be harvested using techniques known to those skilled in the art. Cells from a selected single strain or mixtures of known strains can be treated as needed (e.g., freeze dried with trehalose or glycerol) to preserve viability and are then placed in capsules designed to protect the cells through their passage through the acid stomach (enteric coated capsules).

Cells are ingested in quantities and at intervals determined by the needs of individuals. In some cases a single, or periodic, use may be all that is needed and in other cases regular ingestion (e.g., with meals) may be needed.

The invention further pertains to administration to the human or animal intestinal tract of oxalate-degrading products or enzymes prepared from oxalate reducing organisms such as *O. formigenes* cells or from other sources, or by methods such as by recombinant means. In one embodiment, oxalate degrading enzymes can be purified and prepared as a pharmaceutical or nutriceutical composition for oral consumption. In a preferred embodiment, these enzymes are produced recombinantly. DNA sequences encoding these enzymes are known to those skilled in the art and are described in, for example, WO 98/16632. These sequences, or other sequences encoding oxalate-degrading proteins, can be expressed in a suitable host. The host may be, for example, *E. coli* or *Lactobacillus*. The transformed host would include appropriate regulatory and transporter signals. The expressed protein may be isolated, purified and administered as described herein. Alternatively, the recombinant host expressing the desired oxalate-degrading proteins may be administered. The recombinant host may be administered in either a viable or non-viable form. In another preferred embodiment, the enzymes are coated or otherwise formulated or modified to protect the enzymes so that they are not inactivated in the stomach, and are available to exert their oxalate-degrading activity in the small intestine. Examples of such formulations are known to those skilled in the art and are described in, for example, U.S. Pat. No. 5,286,495.

Oxalate degrading enzymes as used herein include all enzymes involved in oxalate pathways and include but are not limited to, oxalate oxidase, oxalate decarboxylase, formyl CoA transferase and oxalyl-CoA decarboxylase. Oxalate oxidase is expressed in higher plants and it catalyzes the oxygen dependent oxidation of oxalate to $CO_2$ with concomitant formation of $H_2O_2$. Oxalate oxidases have been purified from many sources for example, barley seedlings roots and leaves; beet stems and leaves; wheat germ; sorghum leaves; and banana peel. A rapid three step purification procedure has been developed to obtain oxalate oxidase from barley roots. The gene encoding the barley root oxalate oxidase has been cloned, sequenced and expressed.

Oxalate decarboxylase is mainly present in fungi. A bacterial oxalate decarboxylase has been recently reported in *B. subtilis* and is encoded by the yvrk gene. Oxalate decarboxylases catalyze the degradation of free oxalate to $CO_2$ and formate. This enzyme has been reported in several fungi, including *Myrothecium, verrucaria*, certain strains of *Aspergillus niger*, and white rot fungus, *Coriolus versicolor*. The gene encoding the *Flammulina velutipes* oxalate decarboxylase has been cloned and sequenced; See WO 98/42827.

Oxalyl-CoA decarboxylase is active on a CoA-activated substrate and converts it into formyl-CoA. A formyl-CoA transferase then acts to exchange formate and oxalate on CoA. These enzymes have been studied in the oxalate degrading bacteria, *Pseudomonas oxalaticus* present in the soil and in *Oxalobacter formigenes*, residing in the gastrointestinal tract of vertebrates, including humans. *O. formigenes* has been shown to play a symbiotic relationship with its host by regulating oxalic acid absorption in the intestine as well as oxalic acid levels in plasma. As a result the absence of this bacteria has been found to be a risk factor in oxalate related disorders like recurrent idiopathic calcium oxalate urolithiasis and enteric hyperoxaluria secondary to jejunoileal bypass surgery, cystic fibrosis and inflammatory bowel disease.

Patents describing various oxalate-degrading enzymes and the genes encoding these enzymes include U.S. Pat. Nos. 5,912,125; 6,090,628; and 6,214,980. These patents are incorporated herein by reference in their entirety as if specifically set forth. The term oxalate-degrading enzyme includes but is not limited to oxalate oxidase, oxalate decarboxylase, oxalyl-CoA decarboxylase, and formyl-CoA transferase, and includes enzymes that are capable of interacting with oxalate or oxalic acid. These enzymes may be derived from natural sources or synthesized using recombinant means known in the art, and include all fragments, such as binding sites, active sites, or fragments capable of interacting with oxalate or oxalic acid. This term also includes but is not limited to all necessary cofactors, coenzymes, metals, or binding or substrate materials that are needed by the enzyme in interacting with oxalate or oxalic acid. The present invention also contemplates any binding partners of these enzymes and includes antibodies and antibody fragments that bind to or interact with the enzymes.

The use of *O. formigenes* is particularly advantageous because it is an anaerobe that does not grow in aerobic tissue environments and does not produce any compounds which are toxic to humans or animals. As an alternative to either *O. formigenes* or a recombinant host, other oxalate-degrading bacteria may be used, such as *Clostridium, Bacillus subtilis, Pseudomonas, Lactobacilli, Bifidobacteria*. Oxalate-degrading enzymes prepared from such alternative bacteria may be administered or the entire microbe may be administered.

In addition, all aforementioned embodiments are applicable to domesticated, agricultural, or zoo-maintained animals suffering from deficient numbers of oxalate-degrading bacteria, as well as to humans. For example, oxalate-degrading enzymes and/or microbes may be administered to house pets such as dogs, cats, rabbits, ferrets, guinea pigs, hamsters and gerbils, as well as to agricultural animals, such as horses, sheep, cows and pigs, or wild animals maintained for breeding purposes such as river otters Many animals that are capable of oxalate reduction lose that ability when captured. The present invention comprises methods and compositions for restoring lost or reduced oxalate reducing activity. One aspect of the present invention comprises treating animals retrieved from the wild that have lost or lowered oxalate reducing activity with the compositions taught herein.

The present invention comprises compositions and methods for the administration of compositions comprising one or more oxalate-degrading bacteria, one ore more enzymes, or combinations of bacteria and enzymes, into a human or animal gastrointestinal tract. Such compositions and methods are effective in reducing the amount and/or concentration of oxalate present. Such methods and compositions are effective in treating and preventing oxalate related conditions. An aspect of the present invention comprises compositions and methods for the introduction of oxalate-degrading enzymes into the gastrointestinal tract of a human or animal. The present invention comprises methods for delivering one or more oxalate-degrading enzymes to the gastrointestinal tract of a human or animal as pharmaceutical and/or nutriceutical carrier compositions. Such enzymes include, but are not limited to oxalate oxidase, oxalate decarboxylase, oxalyl-CoA decarboxylase, and formyl-CoA transferase. These enzymes can be derived from sources known to those skilled in the art. For example, the plant enzyme, oxalate oxidase (OXO) can be purified from Barley seedlings, and oxalate decarboxylase can be purified from bacterial or fungal sources.

Alternatively the oxalate-degrading enzymes can be derived by recombinant means. For example, recombinant means such as cloning, expression and purification may be used to obtain oxalate reducing enzymes, for example the *B. subtilis* oxalate decarboxylase enzyme. Such recombinant methods are known to those skilled in the art. For example, disclosed, in general, is the cloning and expression of *B. subtilis* oxalate decarboxylase (YvrK) gene: The gene for oxalate decarboxylase protein (YvrK) has been cloned into the pET-9a and pET-14b plasmid (Novagen, Wis.), under the control of a strong bacteriophage T7 promoter, for overexpression as soluble cytosolic protein. The expression host was the *E. coli* strain BL 21(DE3) pLysS, a λDE3 lysogen deficient in proteases and which contains a chromosomal copy of the T7-RNA polymerase gene under the lacUV5 control. In addition, this strain carries a pET-compatible plasmid that encodes T7 lysozyme, a bifunctional enzyme that cuts a bond in the peptidoglycan layer of the cell wall and inhibits T7 RNA polymerase. This enables greater control of uninduced basal expression and allows the use of methods that disrupt the inner membrane, such as freeze-thaw, or mild detergents, etc.) to efficiently lyse the cell. Expression of the gene product is induced by the addition of isopropyl-β-D-thiogalactopyranoside (IPTG). Accordingly, an aspect of the present invention comprises methods comprising the administration of oxalate-degrading enzymes that have been produced by a recombinant microbe. A variety of expression vectors and hosts can be used to produce oxalate degrading enzymes as recombinant proteins, and such methods are known to those skilled in the art.

Another aspect of the present invention comprises methods for reducing oxalate absorption by supplying oxalate-degrading bacteria to the gastrointestinal tract of a human or animal. Such bacteria may include, but are not limited to, *Oxalobacter formigenes, Clostridium, Lactobacilli, Bifidobacteria* and *Pseudomonas*. *O. formigenes* has been isolated from human fecal specimens and cloned through the selection of individual colonies. This includes the isolate HC-1 which was originally obtained by Ixion Biotechnology in 1996 from Dr. Milton Allison. For example, frozen stocks of human strain HC-1, can be used. Methods of the present invention comprise enriching of the intestines with one or more species of oxalate-degrading bacteria, overall reducing of oxalate in the intestinal contents, reducing oxalate absorption in the intestines, reducing oxalate concentration in blood and renal fluids and reducing the deleterious effects on the body due to the presence of oxalate.

Accordingly, an aspect of the present invention comprises compositions and methods for supplying oxalate-reducing bacteria and oxalate degrading enzymes, that can reduce oxalate to the intestinal tracts of persons having increased risk of oxalate-related diseases and/or conditions. Such diseases and conditions include but are not limited to hyperoxaluria, primary hyperoxaluria, idiopathic calcium oxalate kidney stone disease (urolithiasis), enteric hyperoxaluria, vulvodynia, oxalosis associated with end-stage renal disease, cardiac conductance disorders, inflammatory bowel disease, Crohn's disease, ulcerative colitis, persons having undergone jejunoileal bypass surgery, persons having insufficient concentrations of oxalate-degrading bacteria, and other enteric disease states. Humans and animals that have undergone antibiotic treatment, chemotherapeutic treatment or other treatments that change the intestinal flora are treated with the compositions and methods of the present invention.

The present invention is used to restore oxalate reduction capability to humans or animals with changed intestinal flora. Increased levels of urinary oxalate excretion promote the formation of kidney stones, contribute to renal scarring, and may even result in kidney failure. Accordingly, an aspect of the present invention comprises compositions and methods for reducing the formation of kidney stones.

A reduction in overall oxalate concentrations in the intestines can also lead to removal of oxalate from cells and general circulation. More specifically, a reduction of oxalate concentration in the intestines can also lead to enhanced secretion of oxalate into the intestine from the blood. Though not wishing to be bound by any particular theory, it is currently believed that there is a transepithelial gradient for the enteric elimination of oxalate. Accordingly, an aspect of the present invention comprises compositions and methods for lowering blood levels of oxalate and increasing oxalate excretion by promoting excretion of oxalate from the blood via a transepithelial gradient of oxalate for colonic oxalate excretion. A method of the present invention comprises providing to the intestines of a human or animal a composition for lowering the oxalate concentration or level of a human or animal. Such lowering can comprise lowering of the amount of oxalate found in the intestines, in blood, in serum, in tissue fluids, and in other bodily fluids.

One composition of the present invention comprises an *O. formigenes* paste prepared for oral administration. For each lot of *O. formigenes* paste, a single stock vial of HC-1 is used to generate a seed culture in order to initiate growth in large-scale production fermentation. The bacteria from each fermentation are collected by centrifugation and blended with cryoprotective excipients, which provide protection against freeze-drying. The cell paste can also be subjected to freeze-drying resulting in a fine powder which has a potency in the range of $10^7$ to $10^9$ CFUs/gram. The resulting powder is placed into gelatin capsules that are enteric coated for safe delivery of the bacteria to the small intestine.

Compositions of the present invention comprise compositions made from extracts of one or more oxalate-reducing bacteria in the range from about $10^3$ to about $10^{12}$ cfus/gram, from about $10^3$ to about $10^{10}$ cfus/gram, from about $10^5$ to about $10^{12}$ cfus/gram, from about $10^5$ to about $10^{10}$ cfus/gram, from about $10^7$ to about $10^9$ cfus/gram, from about $10^7$ to about $10^8$ cfus/gram and all ranges in between.

Compositions of the present invention also comprise compositions comprising one or more enzymes that have activity in reducing oxalate. An aspect of the invention comprises administering an effective amount of an enzyme composition to the gastrointestinal tract of a human or animal. An effective amount of an enzyme composition is capable of reducing a portion of oxalate in the intestines or lowering the oxalate concentration in a human or animal from the level measured prior to administering the composition. Such measurement may be a measurement of oxalate present in the gut from food sources or may be a level measured in a body fluid like blood or urine.

The present invention comprises methods for administering compositions containing *O. formigenes* to the gastrointestinal tracts of a human or animal. Subjects are preferably dosed with enteric capsules containing $\geq 10^6$ cfus of viable *O. formigenes* cells. Such dosing preferably occurs twice a day with two major meals. The present invention also comprises methods for administering oxalate reducing compositions comprising one or more oxalate reducing microorganisms, one or more oxalate reducing enzymes or combinations thereof. A method of the present invention comprises administering at least one time a day an effective amount of an oxalate reducing composition wherein the oxalate reducing composition comprises one or more oxalate reducing enzymes. Methods also include administering such compositions more than one time per day, more than two times per day, more than three times per day and in a range from 1 to 15 times per day. Such administrations may be continuously, as in every day for a period of days, weeks, months or years, or may occur at specific times to treat or prevent oxalate-related conditions. For example, a person or animal may be administered oxalate reducing compositions at least once a day for years to treat or prevent oxalate-related conditions or a person or animal may be administered oxalate reducing compositions at least once a day only at times when oxalate-containing foods are ingested, or for a restricted time period, such as days or weeks, following procedures or treatments that interfere with normal bacterial flora. Such administration can occur through routes known for administration of pharmaceuticals. Administration through oral or intestinal routes, or in combination with food materials are contemplated by the present invention.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the forgoing relates only to preferred embodiments of the present invention and that numerous modifications or alterations may be made therein without departing from the spirit and scope of the invention as set forth in this disclosure.

Following are examples which illustrate procedures for practicing the invention. These examples are not to be construed in any way as imposing limitations upon the scope of the present invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Treatment of High Risk Patients

Primary Hyperoxaluric patients were fed enteric coated capsules containing freeze dried powder of *O. formigenes* twice a day preferable with their two big meals of the day. Each size-2 capsule contained about 137 mg of lyophilized bulk powder containing at least $10^8$ Colony Forming Units (CFUs)/gram.

For high risk subjects this may be a life long treatment. Subjects in clinical studies showed that colonization dropped when the treatment was stopped. In the clinical study, treatment was done for 4 weeks and there was a two week follow up. The 4-week treatment resulted in significant decrease in blood and urinary oxalate levels as compared to the baseline levels. But during the follow up period, the stool counts for *Oxalobacter* dropped and the plasma and urine oxalate values started to increase. Thus, it is proposed that continuous feeding of oxalate-reducing compositions will be needed to provide the reduced oxalate conditions. Compositions comprising bacteria that can colonize and establish themselves continuously in the gut could lead to the need for fewer administrations of oxalate-reducing compositions.

Enteric coated capsules of *O. formigenes* cells can be ingested by patient populations at high risk for oxalate related disease. These include:

1. Persons who produce too much endogenous oxalate due to, for example, a genetic defect like Primary Hyperoxaluria
2. Persons at risk for urolithiasis with high urinary oxalate due to enteric disease (enteric-hyperoxaluria).
3. Persons that have a history of urolithiasis with multiple episodes of idiopathic stone disease.
4. Persons with high serum oxalate levels due to end stage renal disease.
5. Persons with vulvar vestibultitis.
6. Persons that have diets with high levels of oxalate such as found in certain areas and seasons in India and in Saudi Arabia. This would also include individuals who happen to prefer foods such as spinach which are high in oxalate.

Anyone of the above described persons or animals are provided a composition of the present invention. For example, a person with higher than normal endogenous oxalate levels is treated two times a day, with a capsule designed for delivery of its contents to the large intestine, wherein the capsule contains approximately $10^6$ cfus of *O. formigenes*. The capsule is preferably given with food.

EXAMPLE 2

Treatment of Low Risk Patients

Enteric protected *O. formigenes* cells, such as provided in enteric coated capsules can also be ingested by individuals in populations at lower risk for oxalate related disease. It would be desired to colonize these patients with one or two treatments comprising compositions of oxalate-reducing materials, such as oxalate-reducing bacteria. These patients could also routinely receive treatments of oxalate-reducing materials, either as supplements or as additions to foods such as milk or yogurt. These include:

1. Persons that have lost populations of normal oxalate degrading bacteria due to: treatments with oral antibiotics or bouts of diarrheal disease.
2. Infants can be inoculated so that a normal protective population of *Oxalabacter* will be more easily established than is the case later in life when competitive exclusion principles operate.

The persons or animals who are low risk are treated two times a day, with a capsule designed for delivery of its contents to the large intestine, wherein the capsule contains at least $10^7$ cfus of one or more oxalate reducing organisms, such as *O. formigenes*. The capsule is preferably given with food.

EXAMPLE 3

Use of Oxalate Degrading Enzymes from *Oxalobacter formigenes* to Control Hyperoxaluria A study was conducted to evaluate the efficacy of oxalate degrading enzymes from *Oxalobacter formigenes* for the control of hyperoxaluria.

Animals Used: Male Sprague Dawley Rats: BW 250-300 g

Diets Used: Normal Diet (N.D.): Harlan Teklad TD 89222; 0.5% Ca, 0.4% P

Drug Used: Lyophilized mixture of *Oxalobacter formigenes* lysate (source of enzymes) with Oxalyl CoA, $MgCl_2$ and TPP.

Drug Delivery System (Capsules): Size 9 capsules for preclinical rat studies (Capsu-Gel). Enteric Coating Eudragit L-100-55 (Hulls America, Inc.). Basal 24 hr urine collection. Fecal analysis for *Oxalobacter formigenes*—rats were not colonized with *Oxalobacter formigenes*.

Experimental Protocol:

A. Long-Term Studies:

Animal Protocol:

Group I (n=4): Fed oxalate diet with lysate. Rats were given two capsules everyday at 4:00 p.m. and oxalate diet overnight. Diet was removed during the day (8:00 a.m. to 4:00 p.m.)

Group II (n=4): Fed oxalate diet as described for Group I (Hyperoxaluric Controls).

24 hr urine samples were collected on Day 7 and Day 9 of the above treatment.

Data on the mean urinary oxalate concentration for the two groups of rats shown above indicated that feeding of *Oxalobacter* lysate lowered the urinary oxalate concentration in Group I rats as compared to the hyperoxaluric controls (Group II). The enzymes can not be active for a long duration in the gastrointestinal tract; therefore, short-term studies were performed as described below.

B. Short-Term Studies:

Animal Protocol:

Group I (n=4): Fed 1 capsule at 8:00 a.m.; oxalate diet for two hours (rats were fasted overnight so that they eat well during this period) and 1 capsule at 10:00 a.m.

Group II (n=4): Oxalate diet for two hours as for Group I.

Urine was collected from all the animals for the next five-hour period and analyzed for oxalate concentration.

This was performed on days 11, 12 and 15 of this study.

The results of this study show that feeding the *Oxalobacter* lysate produces a significant decrease in urinary oxalate levels in a 5 hour period after oxalate and drug administration in Group I rats as compared to the hyperoxaluric control group (Group II). At this point a crossover study between the two groups of rats was performed.

C. Cross-Over Studies:

Animal Protocol:

Group I: Fed oxalate diet twice a day at 8:00-10:00 a.m. and 3:00 p.m-5:00 p.m.

Group II: Fed 1 capsule twice a day before feeding the oxalate diet as for Group I.

Short-term studies for the effect of oxalobacter lysate feeding on urinary oxalate levels were performed as described in Section-B above on day-2 and day-5 after the cross-over.

Crossover studies showed that previously hyperoxaluric Group II rats, which were fed the *Oxalobacter* lysate, showed a decline in urinary oxalate levels. In contrast the Group-I rats reverted to hyperoxaluria upon withdrawal of the drug.

EXAMPLE 4

Treatment with *Oxalobacter formigenes* Cells to Rats

A study was conducted to evaluate the fate of dietary oxalate when *Oxalobacter formigenes* cells are included in the diet.

Methods:

Male Wistar rats were fed a normal calcium (1%), high oxalate (0.5%) diet, or a low calcium (0.02%), high oxalate diet (0.5%) diet during two separate experiments. $^{14}$C-oxalate (2.0 µCi) was given on day 1 and again on day 7 of the study. *Oxalobacter formigenes* cells (380 mg/d) were administered in rat drinking water on days 5-11. The fate of $^{14}$C from oxalate was measured based on analysis of $^{14}$C in feces, urine and expired air. The rats served as self controls and measurements during the control period (before *Oxalobacter* cells were fed) were made during days 1-4; during the experimental period (when bacterial cells were fed) measurements were made on days 7-11.

Figure 1B:
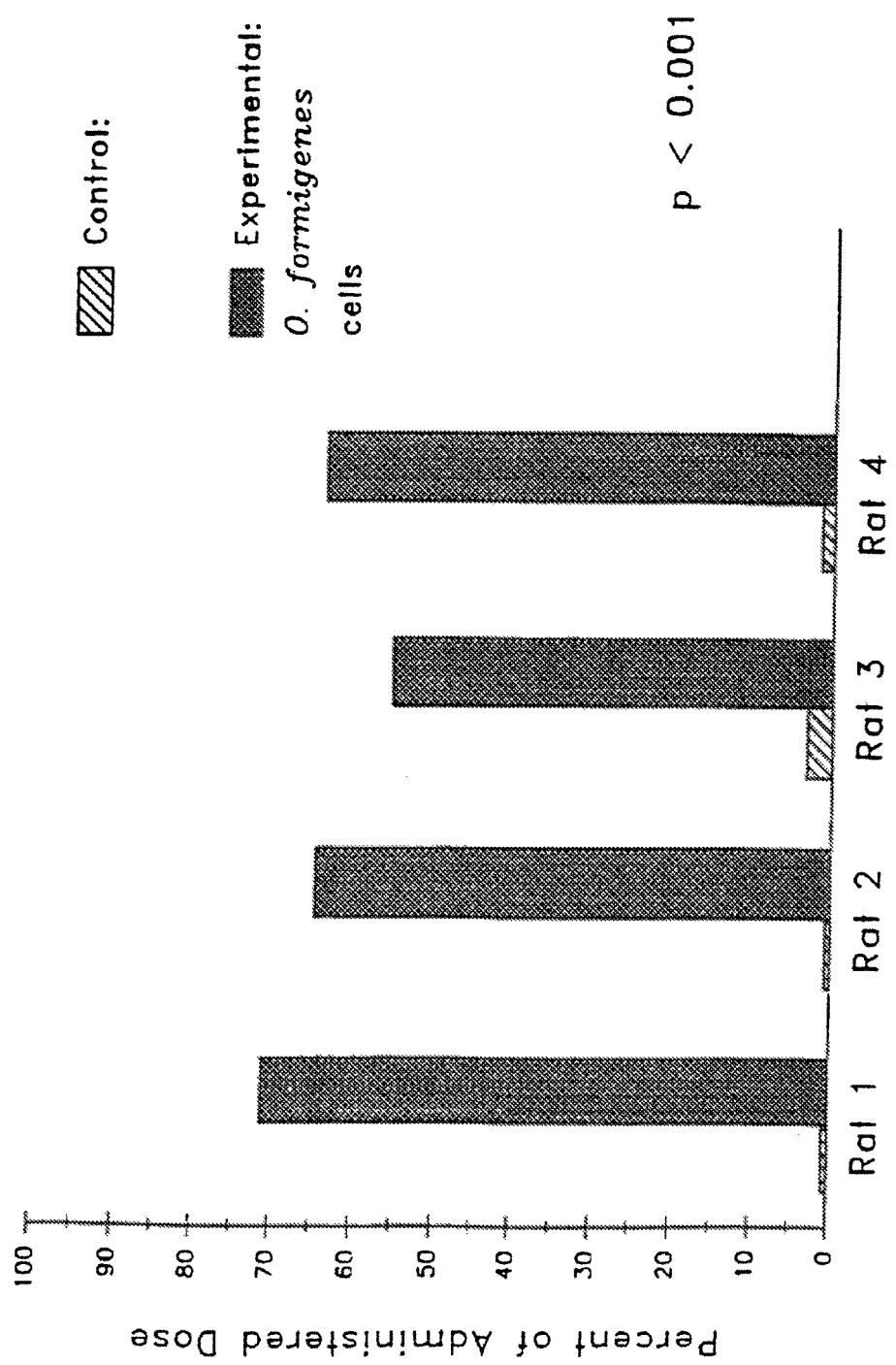
FIG. 1B is a graph of data from a low calcium diet.

Results:

1. When rats were fed the normal (1%) calcium diet, less than 1% of the administered dose of $^{14}$C from oxalate was recovered in expired air (as carbon dioxide produced from $^{14}$C oxalate in the intestine, absorbed into blood and then expired) however in all cases more of the $^{14}$C was recovered during the period when rats were fed *Oxalobacter* cells (FIG. 1*a*) This is in contrast to results obtained when the diet was low in calcium (0.02%) when more than 50% of the $^{14}$C from oxalate was recovered as carbon dioxide in expired air during the experimental period when rats were fed *Oxalobacter* cells (FIG. 1*b*). These results are strikingly different from the very low quantities of $^{14}$C (less than 5%) recovered during the control period (before the feeding of *Oxalobacter* cells). Thus feeding *Oxalobacter formigenes* cells to rats markedly increased the amount of dietary oxalate that was degraded in the intestinal tract.

Figure 2A:
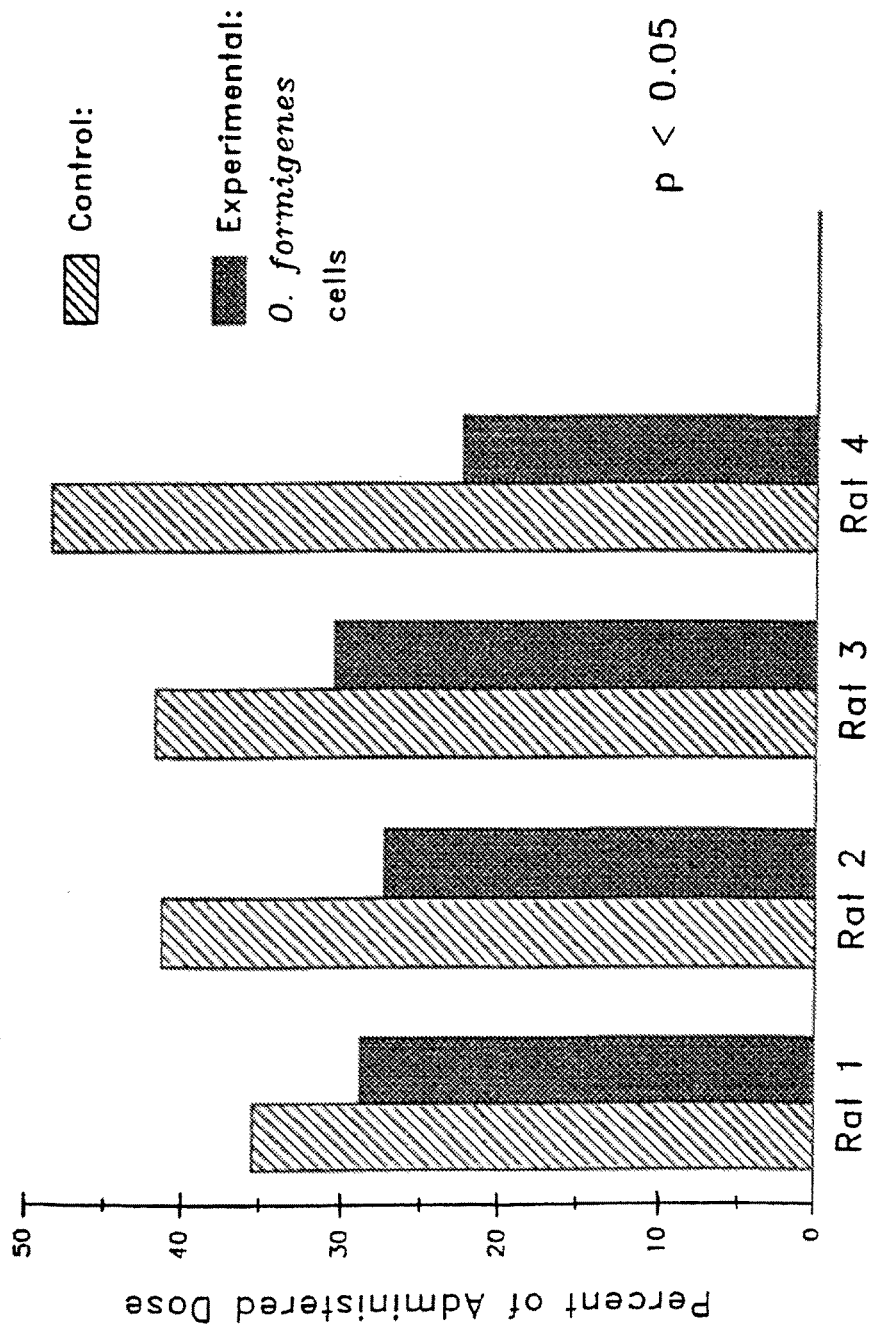
FIG. 2A is a graph of excreted oxalate.
Figure 2B:
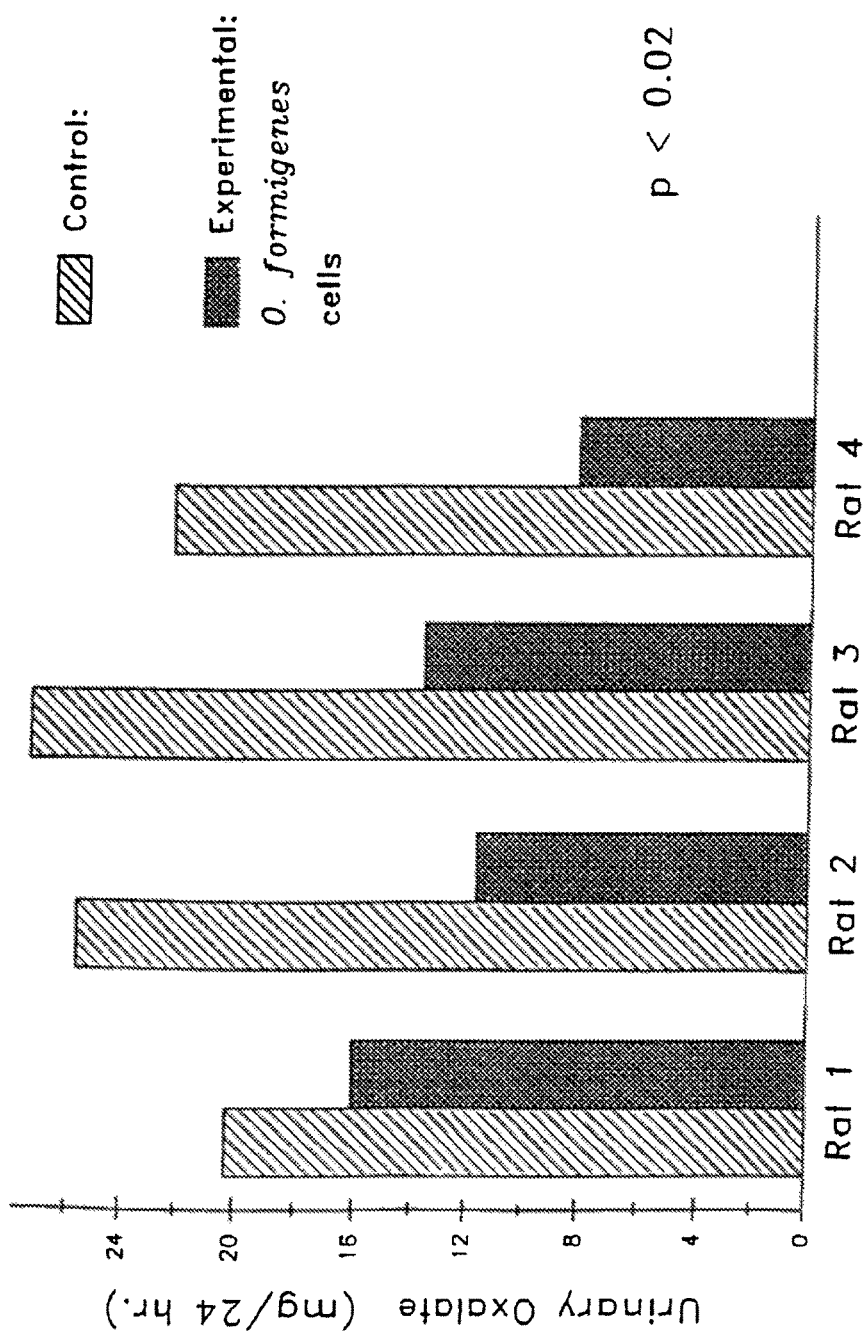
FIG. 2B a graph of excreted oxalate.
Figure 2C:
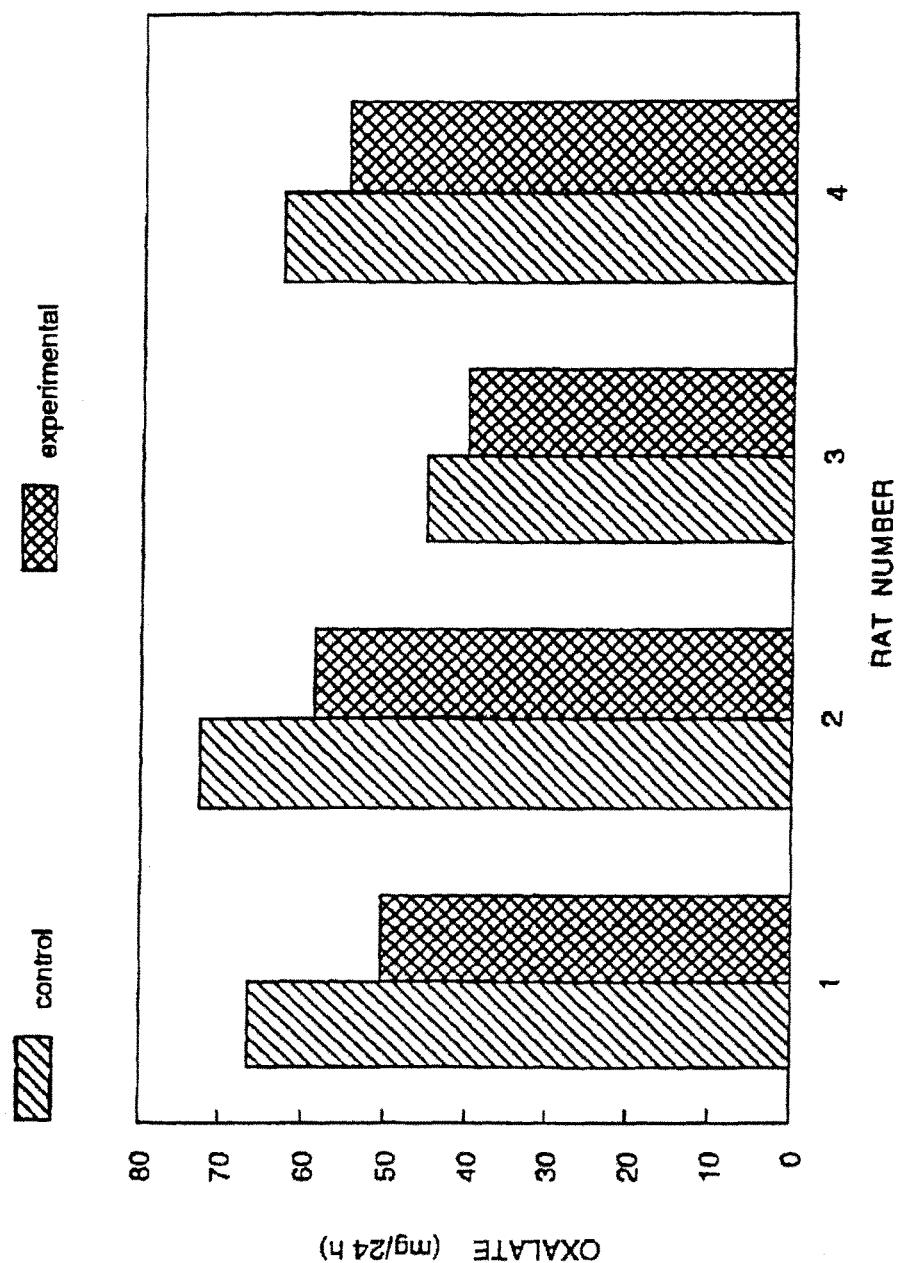
FIG. 2C a graph of excreted oxalate.

2. Feeding *Oxalobacter* cells also decreased the amount of $^{14}$C-oxalate that was excreted in urine. Values for a 4 day collections during both the control and experimental periods and for a single day in each of these periods are shown in FIGS. 2*a* and 2*b* respectively. Quantities of oxalate recovered in rat feces were also lower during the experimental period (when *Oxalobacter* cells were fed) than was found for the control period (FIG. 2*c*).

Most laboratory rats do not carry *Oxalobacter* in their intestinal tracts (they are not colonized). The present results showed that purposeful administration of these oxalate-degrading bacteria to rats caused a large portion of the dietary oxalate to be degraded and that consequently less of the oxalate from the diet was excreted in urine.

The effects of dietary calcium on oxalate degradation are marked. Calcium complexes with oxalate so that its solubility and availability for attack by *Oxalobacter* is limited and the amount that is degraded when rats are fed a high calcium diet is much less than amounts degraded when calcium in the diet is low.

EXAMPLE 5

Effect of Feeding *O. formigenes* on Urinary Oxalate Excretion in Pigs

Figure 3A:
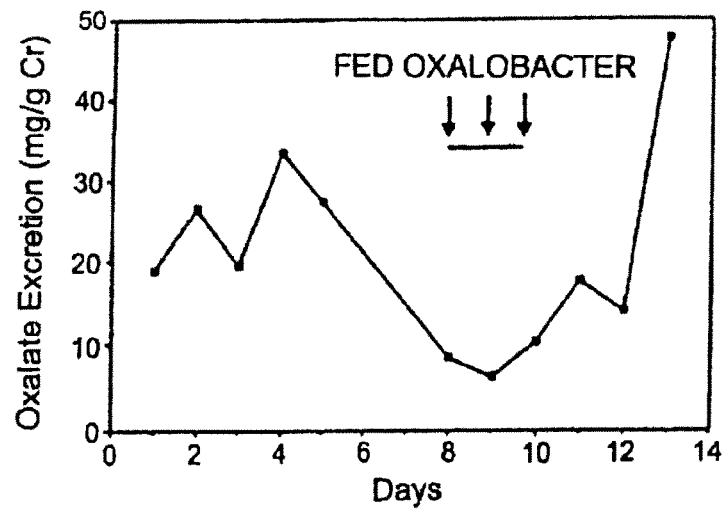
FIGS. 3A-C a graph of excreted oxalate.
Figure 3B:
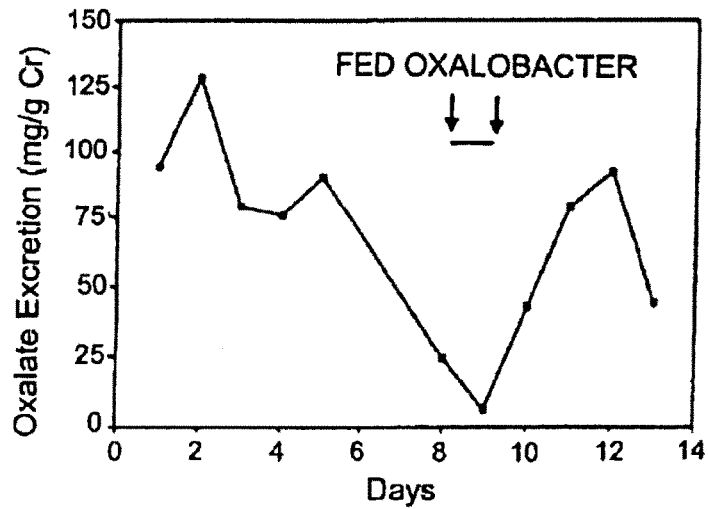
Figure 3C:
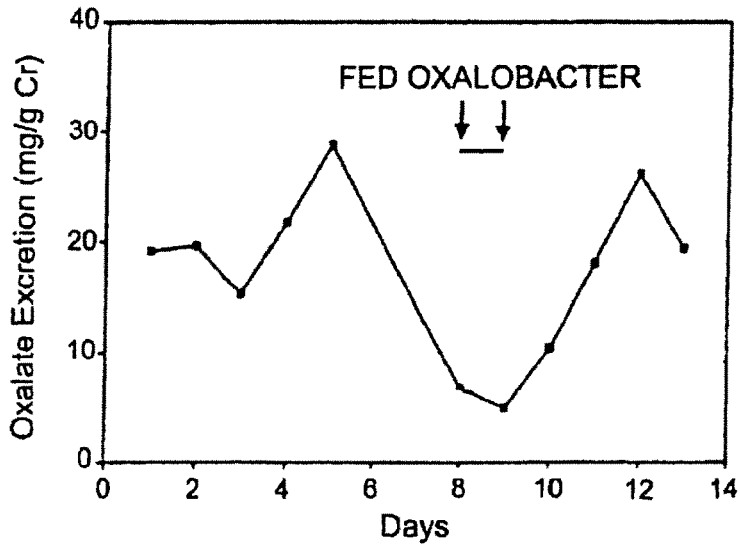

Pigs are naturally colonized with *Oxalobacter*. Decolonization was achieved in experimental pigs by antibiotic supplementation of the diet. Pigs were fed *Oxalobacter* in culture broth, which they readily consumed. The pigs were fed a soybean/corn based feed supplemented with 1300 mg oxalate/kg. The basal diet contained 680 mg oxalate/kg. Results are shown in FIGS. 3*a-c* for three individual pigs.

In all the three pigs urinary oxalate was dramatically decreased during the consumption of *Oxalabacter*. The level of excretion of oxalate in these pigs decreased to a minimum of approximately 6 mg/g creatinine in all three pigs. This is to be compared with a level of 8-10 mg/g creatinine that has been observed in humans taking oxalate-free formula diets. This level is equated to the endogenous synthesis in humans as the dietary load has been eliminated. It appears that this level reflects endogenous synthesis in pigs and that the intestinal absorption has been eliminated by *Oxalobacter* treatment. Furthermore, these results indicate that the ingested *Oxalobacter* were able to remove both the crystalline oxalate added and the food-borne oxalate that was bioavailable.

In this experiment each pig was fed 1.0 g of cell paste with the morning meal. At $O.D_{600}$ of 0.6, viable cell count is $2.1 \times 10^8$ cells/ml, which extrapolates to $2.1 \times 10^{13}$ cells per 100 L. The 100 L fermenter run provides us on the average 50-60 gm wet wt of cells. Therefore, 1 gm wet wt of cells is about $3.5 \times 10^{11}$ viable cells.

The dose of $3.5 \times 10^{11}$ viable cells as indicated above could eliminate intestinal absorption of about 2.0 gm of oxalate present per kg diet (1300 mg added oxalate+680 mg present in the diet). The animals consumed 1 kg diet per meal.

The body weight of the pigs is about 200 lbs. and the digestive system of the pigs is believed to be very close to that of humans. In humans the average daily consumption of oxalate is about 100-400 mg depending on the diet composition which is also split into three meals/day, therefore on an average a daily dose of $10^8$ to $10^{10}$ viable cells would be sufficient to prevent the dietary absorption of oxalate.

EXAMPLE 6

Effect of *O. formigenes* Supplementation on Urinary Oxalate Excretion in Rats Fed High Oxalate Diet A study was conducted to determine the effect of the IxOC-3 formulation on colonization status and urinary oxalate levels following a high oxalate diet. An IxOC-3 formulation comprises freeze-dried viable cells of an oxalate reducing bacteria, such as *O. formigenes*. The formulation contains approximately $10^6$-$10^7$ cfus/gram per dose. The formulation also comprises cyropreservation agents such as trehelose and maltodextrin.

Methods:

Male Harlan Sprague Dawley rats were randomly assigned to 3 groups (6 animals/group). Animals of group 1 served as the control group and were administered size 9 enteric coated placebo formulation twice daily by oral gavage at a dose level of $10^0$ colony forming units (CFU). Animals of Groups 2 and 3 were administered *Oxalobacter formigenes* IxOC-3 formulation in size 9 enteric coated capsule form twice daily by oral gavage at dose levels of $10^6$ and $10^7$ CFUs respectively. Capsule gavage was followed by an autoclaved tap water wash down for all three groups. Following an initial acclimatization period, all groups were feed a standard diet supplemented with 1% oxalate per gram.

Test materials and the placebo control material were prepared following a standardized protocol. Prior to use, representative samples of each test material were analyzed to confirm identity, purity, and potency of the test capsules, as well as to confirm the absence of *Oxalobacter formagenes* in the placebo control material during the dosing period.

Diet was restricted to two daily 1 hour periods starting 15 minutes following morning and evening gavage to ensure capsules were dosed on an empty stomach. Water was provided ad libitum. Food consumption was recorded twice daily. Fecal and 24 hour urine samples were collected at Day 1 (prior to oxalate supplemented diet) and weekly thereafter. The urine data was analyzed via a repeated measures analysis for differences in mean urinary parameters across dosage groups and time. A dosage group by time interaction term was also included to assess any possible interaction between dosage group and time.

Results:

The results of the analysis indicated there was a statistically significant interaction between dose groups and time (p<0.0001) for all parameters indicating that the urinary parameter profile across time was different across the dosage groups. To aid in the interpretation of this interaction, an analysis of the data was conducted by time point for each parameter to determine if there was a difference between the dosage groups with respect to the mean urinary parameters. This analysis revealed that for the low dose and high dose groups, there was an increase in urinary oxalate from baseline to 7 days (p<0.0001 both groups) but there was no increase from 7 days to 28 days (p=0.1094 low dose and p=0.6910 high dose). For the placebo group, however, there was an increase from baseline to 28 days (p=0.0010). Also at day 21 and day 28, mean urinary oxalate levels in the placebo Group I were significantly higher than those for the low (Group II) and high (Group III) dose groups, but no significant difference between the low dose and the high dose. Thus, there was an overall significant decrease in urinary oxalate excretion in treated rats as compared to rats that were fed the placebo.

EXAMPLE 7

The Effects of Oral Administration of *O. formigenes* on Urinary Oxalate Levels in Patients Suffering from Primary Hyperoxaluria (PH)

Methods:

Nine patients with biopsy proven primary hyperoxaluria (PH) participated in the study. After receiving initial baseline evaluations, all subjects were administered *Oxalobacter formigenes* 1 g cell paste ($\geq 10^{10}$ cfus/gram) bid with their main meals for 4 weeks. During this time period, all patients continued to take their normal medication, were asked to eat their normal diet, and to keep their fluid intake as high as normal. Except for spinach and rhubarb, foods high in oxalate were not forbidden. *Oxolobacter* colonization and its influence on urinary and oxalate plasma levels were measured in weeks 5 and 6. Teatment efficacy was followed in terms of urinary oxalate excretion in subjects with normal renal function and plasma oxalate in subjects with end-stage renal disease (ESRD).

Results:

1. Treatment demonstrated a significant lowering of urinary oxalate in subjects with normal urine function. Plasma oxalate decreased significantly in seven out of nine subjects. There was a dramatic lowering of plasma oxalate in two subjects with ESRD providing evidence for enteric elimination of endogenous oxalate into the gut against a transepithelial gradient.

2. Consumption of *O. formigenes* strain HC-1 at dosages ranging from 0.25 g to 2.0 g per meal were well tolerated by normal, healthy volunteers receiving diets containing average or high oxalate levels. A dosage of 1.0 gm cell paste twice a day for 28 days was well tolerated by PH patients.

EXAMPLE 8

Treatment of High Risk Patients with Oxalate Reducing Enzyme Compositions

Primary hyperoxaluric patients are fed one or more enteric coated capsules containing a lyophilized oxalate-reducing enzyme composition, comprising oxalate decarboxylase and/or oxalate oxidase, twice a day preferable with the two main meals of the day. An effective amount of the enzyme composition is administered. For example, each size-2 capsule contains about 5-100 units of each enzyme.

For high risk subjects this is a continuous administration for an extended period of time, probably a life long treatment. Colonization will drop when the treatment is stopped.

Enteric coated capsules of oxalate reducing compositions comprising oxalate reducing enzymes can be administered to patient populations at high risk for oxalate related disease. These include:

1. Persons who produce too much endogenous oxalate due to, for example, a genetic defect like Primary Hyperoxaluria
2. Persons at risk for urolithiasis with high urinary oxalate due to enteric disease (enteric-hyperoxaluria).
3. Persons that have a history of urolithiasis with multiple episodes of idiopathic stone disease.
4. Persons with high serum oxalate levels due to end stage renal disease.
5. Persons with vulvar vestibultitis.
6. Persons that have diets with high levels of oxalate such as found in certain areas and seasons in India and in Saudi Arabia. This would also include individuals who happen to prefer foods such as spinach which are high in oxalate.

Anyone of the above described persons or animals are provided a composition of the present invention. For example, a person with higher than normal endogenous oxalate levels is treated two times a day, with a capsule designed for delivery of its contents to the large intestine, wherein the capsule contains approximately an equivalent effective amount of an enzyme composition having enzyme activity similar to that provided by $10^7$ cfus of an oxalate-reducing bacterium, such as *O. formigenes*. The capsule is preferably given with food.

EXAMPLE 9

Treatment of Low Risk Patients with Oxalate Reducing Enzyme Compositions

Enteric protected oxalate reducing compositions comprising a mixture of the oxalate reducing enzymes oxalate decarboxylase and/or oxalate oxidase, such as provided in enteric coated capsules can also be administered to individuals in populations at lower risk for oxalate-related disease or at risk for oxalate-related conditions. An effective amount of the enzyme composition is administered in the desired treatment regimen.

It would be desired to administer the compositions to these patients either for shorter periods of time when they are at risk for oxalate-related conditions or simultaneously with materials that contribute to oxalate-related condition. These patients could also routinely receive treatments of oxalate-reducing compositions, either as supplements or as additions to foods such as milk or yogurt. These include persons that have lost populations of normal oxalate degrading bacteria due to: treatments with oral antibiotics or bouts of diarrheal disease, or infants.

The persons or animals who are low risk are treated two times a day, with a capsule designed for delivery of its contents to the large intestine, wherein the capsule contains an effective amount of the enzyme composition. For example, each size-2 capsule contains about 5-100 units of each enzyme. The capsule is preferably given with food.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for reducing systemic circulating oxalate in a subject in need thereof, comprising orally administering to a human or animal an effective amount of a composition comprising viable bacterial cells of *Oxalobacter formigenes*, wherein the administering is effected at least once per day for a period of months or years, and wherein the method is effective to induce enteric elimination of systemic circulating oxalate.

2. The method of claim 1, wherein the method is effective to reduce serum levels of oxalate.

3. The method of claim 1, wherein the method is effective to reduce blood levels of oxalate.

4. The method of claim 1, wherein the subject is suffering from an oxalate-related condition.

5. The method of claim 4, wherein the subject is suffering from an oxalate-related condition selected from the group consisting of hyperoxaluria, primary hyperoxaluria, idiopathic calcium oxalate kidney stone disease, urolithiasis, enteric hyperoxaluria, vulvodynia, and oxalosis associated with end-stage renal disease.

6. The method of claim 1, wherein the composition further comprises oxalate-reducing enzymes selected from the group consisting of oxalate oxidase, oxalate decarboxylase, oxalyl-CoA decarboxylase, formyl-CoA transferase, and combinations of any two or more thereof.

7. The method of claim 6, wherein the oxalate-reducing enzymes are produced recombinantly.

8. The method of claim 1, wherein the composition further comprises one or more components selected from the group consisting of coenzymes, cofactors, substrates, and substituents of oxalate degradation pathways.

9. The method of claim 1, wherein the composition is provided with an enteric coating.

10. The method of claim 1, wherein the systemic circulating oxalate is endogenous oxalate.

* * * * *

UNITED STATES PATENT AND TRADEMARK OFFICE
CERTIFICATE OF CORRECTION

PATENT NO. : 10,149,866 B2
APPLICATION NO. : 13/919266
DATED : December 11, 2018
INVENTOR(S) : Sidhu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 498 days.

Signed and Sealed this
Twenty-ninth Day of October, 2019

Andrei Iancu
*Director of the United States Patent and Trademark Office*